(12) United States Patent
Gertych et al.

(10) Patent No.: US 10,733,417 B2
(45) Date of Patent: Aug. 4, 2020

(54) AUTOMATED DELINEATION OF NUCLEI FOR THREE DIMENSIONAL (3-D) HIGH CONTENT SCREENING

(71) Applicant: Cedars-Sinai Medical Center, Los Angeles, CA (US)

(72) Inventors: Arkadiusz Gertych, El Segundo, CA (US); Beatrice Knudsen, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 15/565,677

(22) PCT Filed: Apr. 22, 2016

(86) PCT No.: PCT/US2016/029023
§ 371 (c)(1),
(2) Date: Oct. 10, 2017

(87) PCT Pub. No.: WO2016/172612
PCT Pub. Date: Oct. 27, 2016

(65) Prior Publication Data
US 2018/0075279 A1 Mar. 15, 2018

Related U.S. Application Data

(60) Provisional application No. 62/151,719, filed on Apr. 23, 2015.

(51) Int. Cl.
*G06K 9/00* (2006.01)
*G01N 1/30* (2006.01)
*G01N 33/50* (2006.01)

(52) U.S. Cl.
CPC ............. *G06K 9/0014* (2013.01); *G01N 1/30* (2013.01); *G01N 33/5011* (2013.01)

(58) Field of Classification Search
CPC ..... G01N 1/30; G01N 33/5011; G06K 9/0014
See application file for complete search history.

(56) References Cited

U.S. PATENT DOCUMENTS 6,519,355 B2   2/2003 Nelson et al.
7,756,305 B2 * 7/2010 Price ................. G01N 21/6458
                                              128/922

(Continued)

FOREIGN PATENT DOCUMENTS

WO   2015044419 A1   4/2015
WO   2016172612 A1   10/2016

OTHER PUBLICATIONS

M. Veta et al, Marker-controlled watershed segmentation of nuclei in H&E stained breast cancer biopsy images, Mar. 30-Apr. 2, 2011, IEEE International Symposium on Biomedical Imaging:From Nano to Macro, 618-621 (Year: 2011).*

(Continued)

Primary Examiner — Gregory M Desire
(74) Attorney, Agent, or Firm — Nixon Peabody LLP

(57) ABSTRACT

In various embodiments, the invention teaches systems and methods for analyzing an image of cells, including an image obtained by confocal microscopy, and delineating cell nuclei in the image. In some embodiments, the systems and methods apply a three-dimensional (3-D) radial symmetry transform followed by adaptive post processing of symmetry images to arrive at a mask of seeds that can guide watershed-based segmentation.

13 Claims, 12 Drawing Sheets

(56) References Cited

U.S. PATENT DOCUMENTS

| | | | | |
|---|---|---|---|---|
| 7,760,927 | B2* | 7/2010 | Gholap | G06K 9/00127 |
| | | | | 382/133 |
| 7,817,841 | B2* | 10/2010 | Padfield | G06K 9/0014 |
| | | | | 382/133 |
| 7,833,728 | B2* | 11/2010 | Pastorek | C07K 16/32 |
| | | | | 435/7.1 |
| 7,881,532 | B2 | 2/2011 | Zahniser et al. | |
| 8,116,551 | B2* | 2/2012 | Gallagher | G06K 9/0014 |
| | | | | 382/133 |
| 8,548,745 | B2* | 10/2013 | Callahan | G06K 9/00 |
| | | | | 382/133 |
| 8,712,139 | B2* | 4/2014 | Rittscher | G06K 9/0014 |
| | | | | 382/133 |
| 8,934,698 | B2 | 1/2015 | Wirtz et al. | |
| 9,286,505 | B2 | 3/2016 | Ajemba et al. | |
| 9,292,933 | B2 | 3/2016 | Madabhushi et al. | |
| 9,733,460 | B2* | 8/2017 | Kang | G02B 21/0064 |
| 2002/0150285 | A1 | 10/2002 | Nelson et al. | |
| 2005/0254546 | A1 | 11/2005 | Rittscher et al. | |
| 2005/0265588 | A1* | 12/2005 | Gholap | G06K 9/00127 |
| | | | | 382/128 |
| 2008/0124735 | A1 | 5/2008 | Schuster et al. | |
| 2009/0081775 | A1 | 3/2009 | Hodneland et al. | |
| 2011/0206250 | A1* | 8/2011 | McGinnis | G06T 7/0012 |
| | | | | 382/128 |
| 2011/0318732 | A1 | 12/2011 | Singer et al. | |
| 2013/0094750 | A1* | 4/2013 | Tasdizen | G06K 9/0014 |
| | | | | 382/134 |
| 2018/0075279 | A1* | 3/2018 | Gertych | G01N 1/30 |

OTHER PUBLICATIONS

Bahram Parvin et al, Iterative Voting for Inference of Structural Saliency and Characterization of Subcellular Events, Mar. 2007, IEEE Transactions on Image Processing, vol. 16, No. 3, pp. 615-623 (Year: 2007).*

International Preliminary Report on Patentability for PCT/US2016/029023 dated Nov. 2, 2017, 8 pages.

International Search Report and Written Opinion for PCT/US2016/029023 dated Jul. 29, 2016, 8 pages.

Gertych et al., Automated Detection of Dual p16/Ki67 Nuclear Immunoreactivity in Liquid-Based Pap Tests for Improved Cervical Cancer Rish Stratification, Ann. Biomed Eng., 2012, vol. 40(5), pp. 1192-1204.

Huang et al., Watersheds-Based Segmentation Integrated with Edge Detection, Proc. Of Spie, 2009, vol. 7492, pp. 749208-1-749208-9.

Koyuncu et al., Smart Markers for Watershed-Based Cell Segmentation, PLoS One, 2012, vol. 7(11), pp. 1-11.

Lin et al., Automated Image Analysis Methods for 3-D Quantification of the Neurovascular Unit from Multichannel Confocal Microscope Images, Cytometry Part A, 2005, vol. 66A, pp. 9-23.

Nanni et al., Weighted Fusion of Shape Descriptor for Robust Shape Classification, International Journal of Computer Research 2014, vol. 22(4), pp. 329-359.

Qin et al., Computerized Delineation of Nuclei in Liquid-Based Pap Smears Stained with Immunohistochemical Biomarkers, Clinical Cytometry, Cytometry Part B, 2015, vol. 88B, pp. 110-119.

Wahlby et al., Combining Intensity, Edge and Shape Information for 2D and 3D Segmentation of Cell Nuclei in Tissue Sections, Journal of Microscopy, 2004, vol. 215(1), pp. 67-76.

Supplemental European Search Report EP16784018.0 dated Nov. 14, 2018, 8 pages.

Loy et al., Fast radial symmetry for detecting points of interest, IEEE Transactions on Pattern Analysis and Machine Intelligence, IEEE Computer Society, 2003, 25(8):959-973.

Kuijf et al., Efficient detection of cerebral microbleeds on 7.0 T MR images using the radial symmetry transform, NeuroImage, 2012, 59(3):2266-2273.

Beucher et al., The morphological approach to segmentation: The watershed transformation, mathematical morphology in image processing, 1993, pp. 433-481.

* cited by examiner

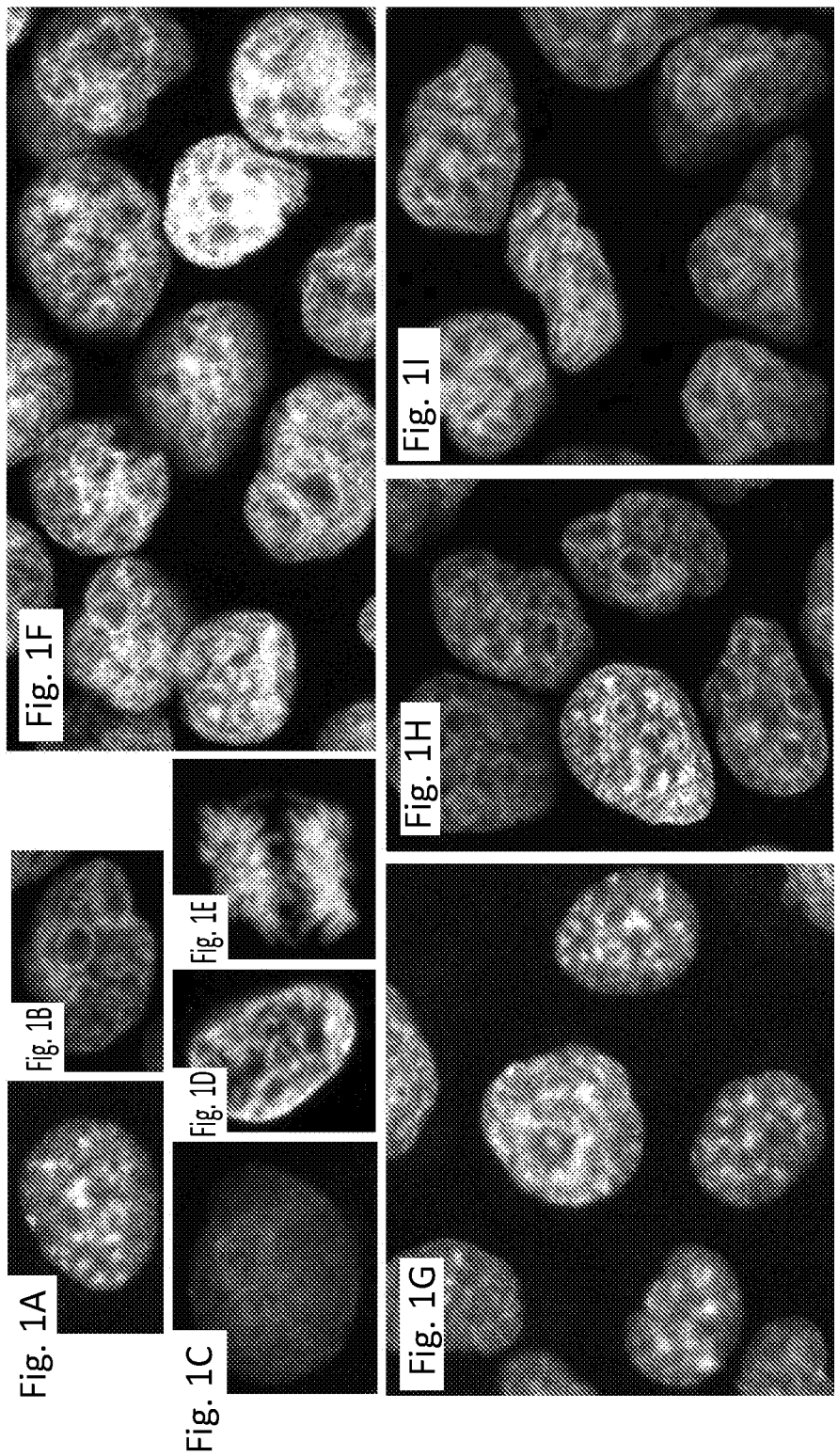

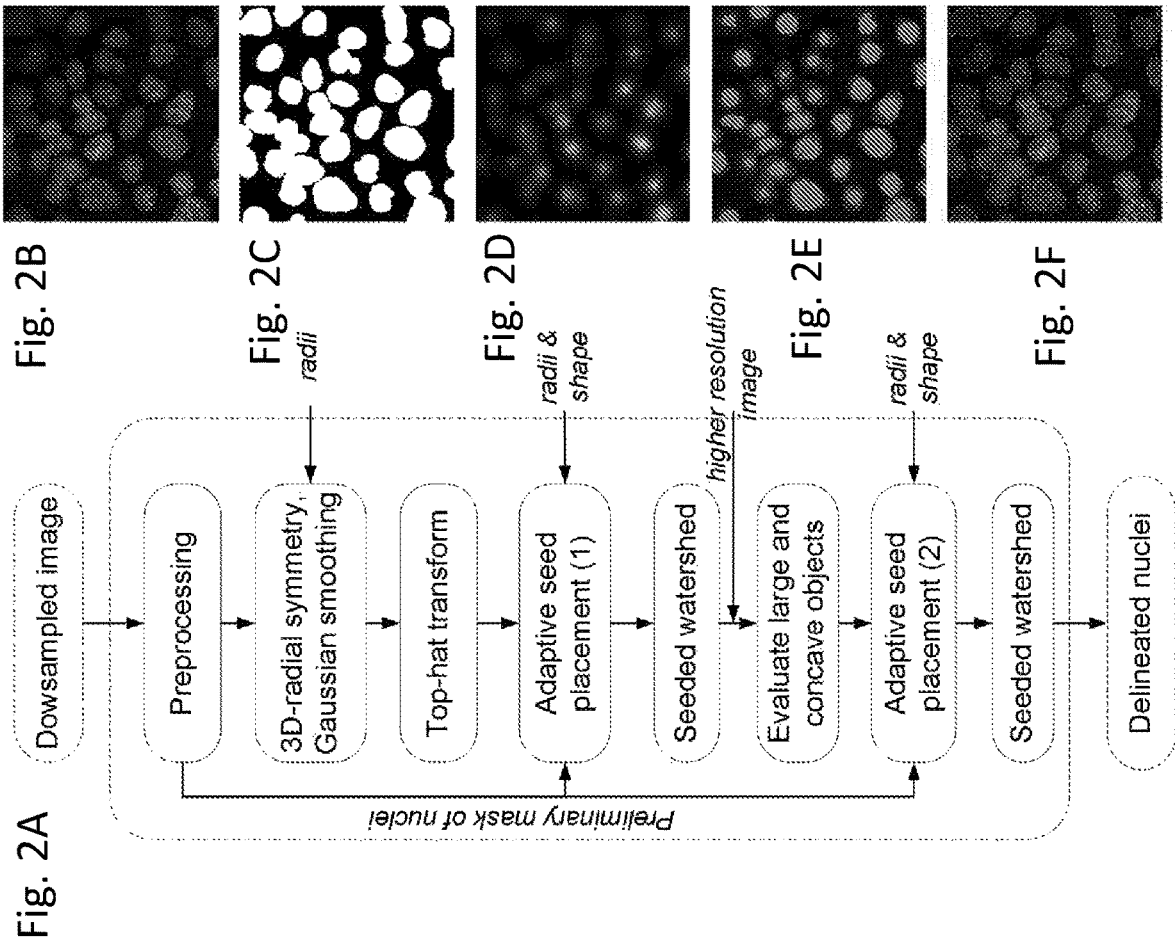

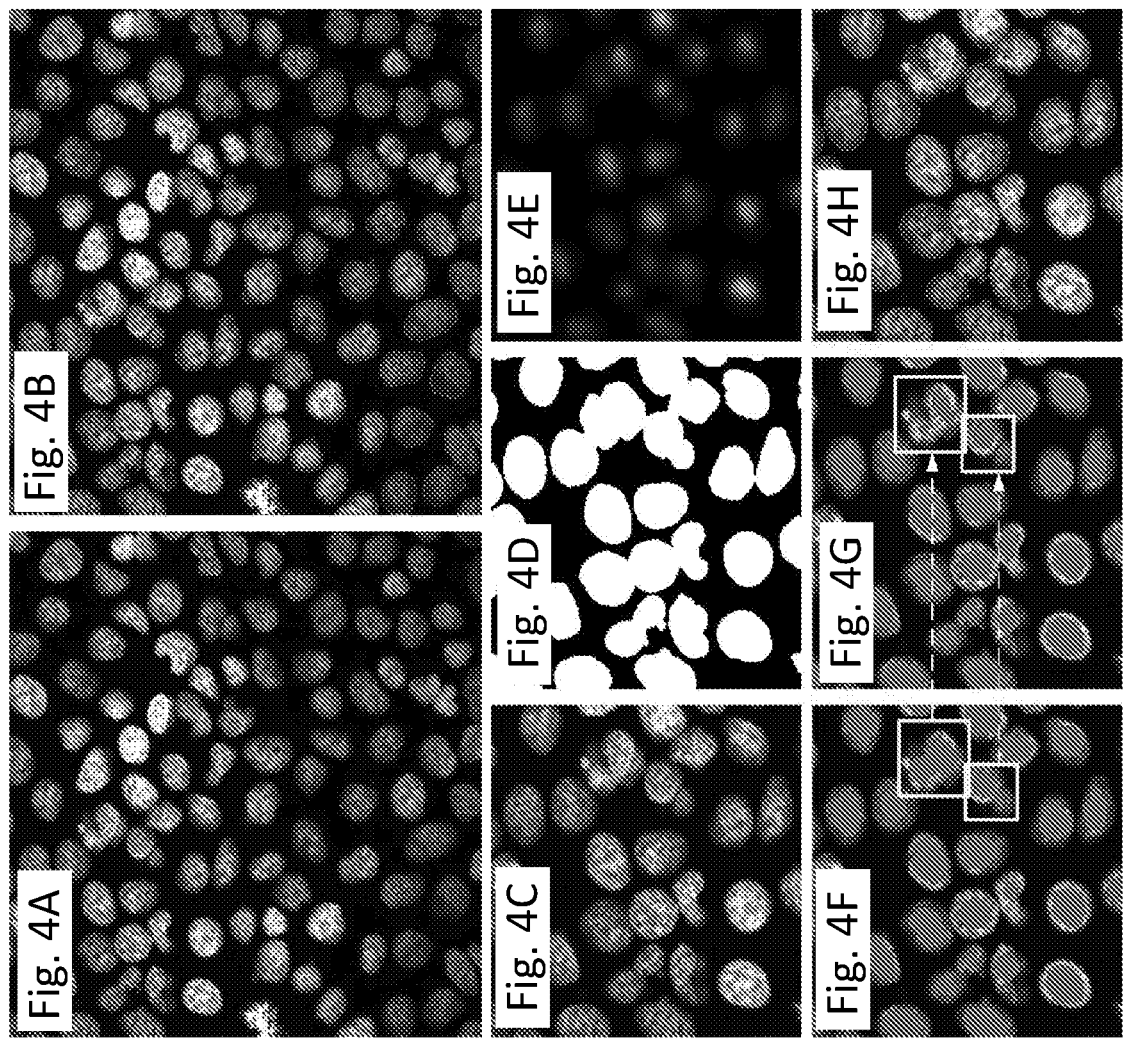

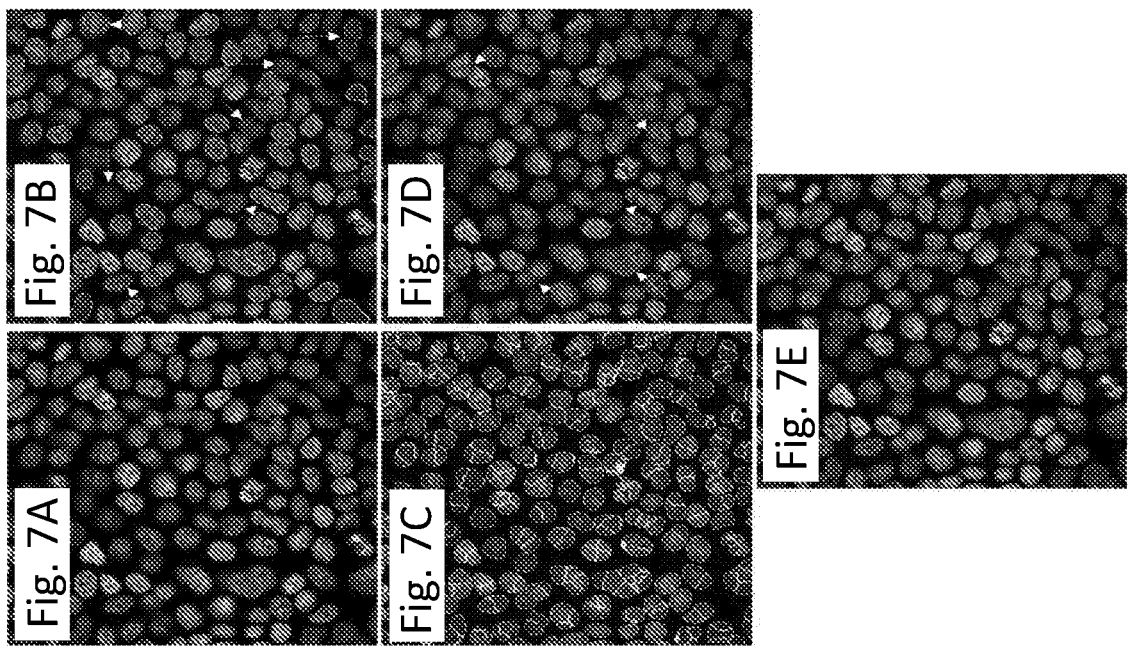

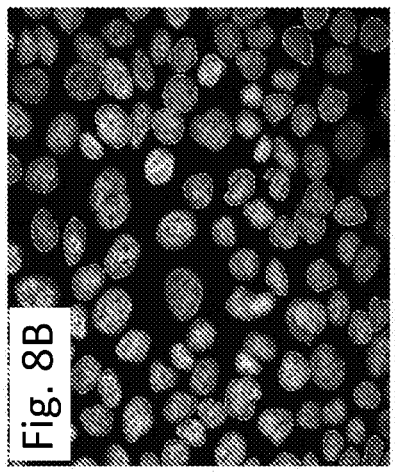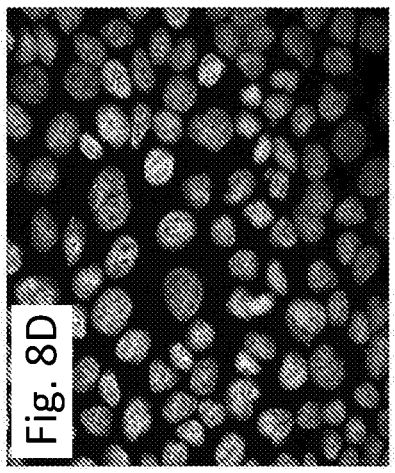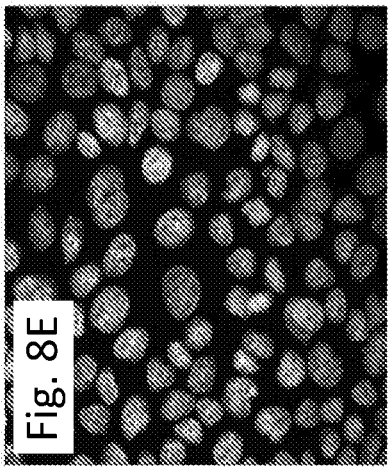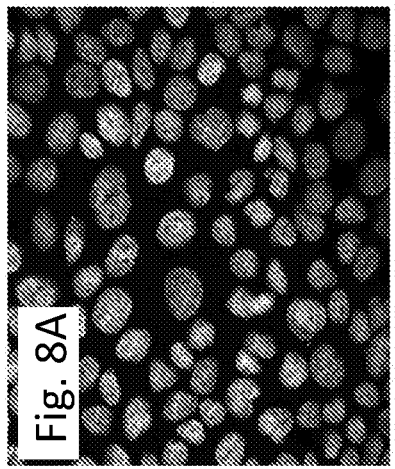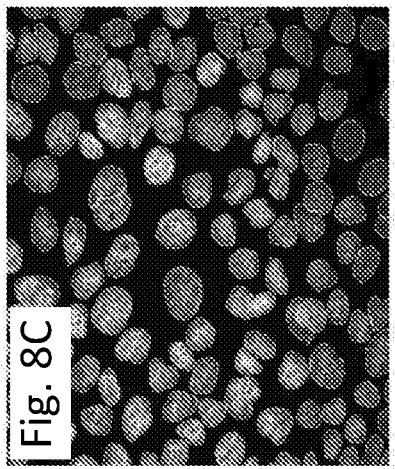

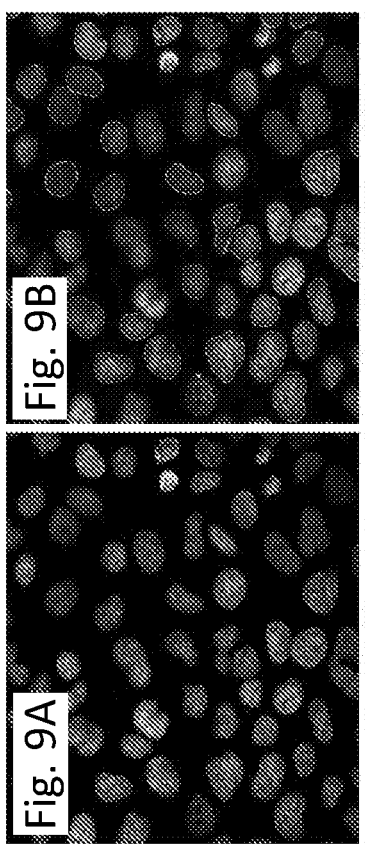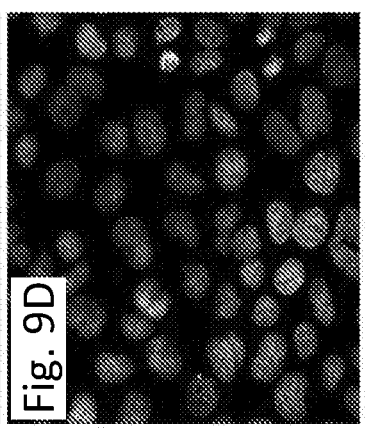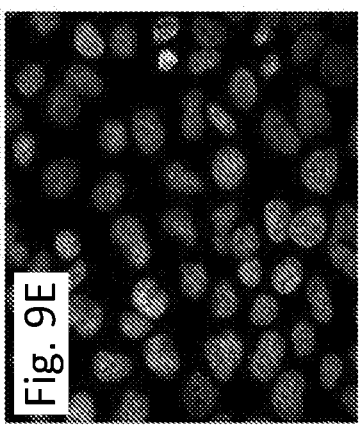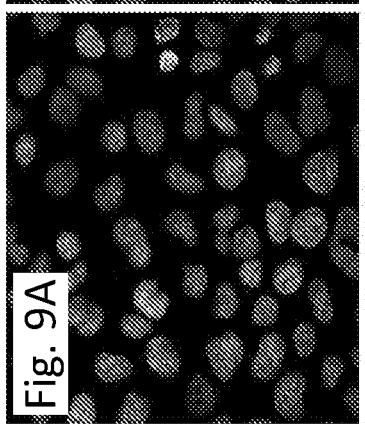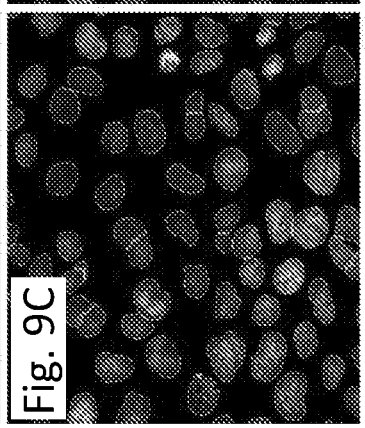

AUTOMATED DELINEATION OF NUCLEI FOR THREE DIMENSIONAL (3-D) HIGH CONTENT SCREENING

CROSS-REFERENCE TO RELATED APPLICATIONS

This application is a National Phase of International Application No. PCT/US2016/029023 filed Apr. 22, 2016, currently pending, which designated the U.S. and that International Application was published under PCT Article 21(2) in English, which also includes a claim of priority under 35 U.S.C. § 119(e) to U.S. provisional patent application No. 62/151,719 filed Apr. 23, 2015, now expired, the entirety of which is hereby incorporated by reference.

GOVERNMENT RIGHTS

The invention was made with government support under Grant No. CA143618 awarded by National Institutes of Health. The government has certain rights in the invention.

FIELD OF THE INVENTION

The present invention generally relates to systems and methods for image processing.

BACKGROUND

High-resolution three-dimensional (3-D) microscopy combined with multiplexing of fluorescent labels allows high-content analysis of large numbers of cell nuclei. The full automation of 3-D screening platforms necessitates image processing algorithms that can accurately and robustly delineate nuclei in images with little to no human intervention. Imaging-based high-content screening was originally developed as a powerful tool for drug discovery. However, cell confluency, complexity of nuclear staining as well as poor contrast between nuclei and background result in slow and unreliable 3-D image processing and therefore negatively affect the performance of studying a drug response. There is clearly a need in the art for improved systems and methods for analyzing images of cells.

SUMMARY OF THE INVENTION

In various embodiments, the invention teaches a method that includes delineating a nucleus of one or more cells in an image of one or more cells by utilizing a mathematical algorithm that is sensitive to the spherical shape of a nucleus of one or more cells in the image. In some embodiments, the method further includes positioning a seed within one or more cell nucleus in the image. In certain embodiments, the seed is obtained through a radial symmetry image that is a weighted sum of orientation projection and magnitude projection images derived from local image gradients. In some embodiments, the method further includes applying watershed-based segmentation in which the positions of two or more seeds is considered during segmentation. In certain embodiments, one or more of the one or more cells have been stained with one or more markers. In some embodiments, one or more of the markers are fluorescent biomarkers. In certain embodiments, one or more of the fluorescent biomarkers are immunofluorescent biomarkers. In some embodiments, at least one cell in the image has been immunolabeled with a 5-methylcytosine antibody and/or 4'6-diamidino-2-phenylindole (DAPI). In certain embodiments, the image is acquired by confocal microscopy. In some embodiments, the image includes cells from a preparation of a tissue mounted on a slide. In some embodiments, at least one cell in the image is a cancer cell or a pre-cancerous cell. In certain embodiments, at least one cell in the image has been treated with a drug. In some embodiments, the drug is a chemotherapeutic drug.

In various embodiments, the invention teaches a non-transitory computer-readable medium storing computer-readable instructions that, when executed by a processor of a computing device causes the computing device to perform steps that include delineating a nucleus of one or more cells in an image of one or more cells by utilizing a mathematical algorithm that is sensitive to the spherical shape of a nucleus of one or more cells in the image. In some embodiments, the steps further include positioning a seed within one or more cell nucleus in the image. In certain embodiments, the seed is obtained through a radial symmetry image that is a weighted sum of orientation projection and magnitude projection images derived from local image gradients. In some embodiments, the steps further include applying watershed-based segmentation in which the positions of two or more seeds is considered. In certain embodiments, one or more of the one or more cells has been stained with one or more markers. In some embodiments, one or more of the markers are fluorescent biomarkers. In certain embodiments, at least one cell in the image has been immunolabeled with a 5-methylcytosine antibody and/or 4'6-diamidino-2-phenylindole (DAPI). In certain embodiments, the image is acquired by confocal microscopy. In some embodiments, the image includes cells from a preparation of tissue mounted on a glass slide. In certain embodiments, at least one cell in the image is a cancer cell or pre-cancerous cell. In some embodiments, at least one cell in the image has been treated with a drug.

BRIEF DESCRIPTION OF THE DRAWINGS

Exemplary embodiments are illustrated in the referenced figures. It is intended that the embodiments and figures disclosed herein are to be considered illustrative rather than restrictive.

FIG. 1A-FIG. 1I depict, in accordance with an embodiment of the invention, patterns of nuclear staining, confluency and cell types encountered in the datasets: FIG. 1A) speckled, FIG. 1B) nucleolar, FIG. 1C) low intensity, FIG. 1D) high intensity, FIG. 1E) mitotic, FIG. 1F) high confluency area (about 65%), and G) DU145 untreated cells in a low confluency area (about 27%), H) DU145 treated cells, and I) HuH-7 treated cells. All cells were prepared using the same staining protocol, as described herein, and all images were acquired using the same microscope settings, and were recorded in 3-D using a 63× objective. Note changes in nuclear patterns and shape in FIG. 1A) vs. FIG. 1B) and FIG. 1C) induced by drug treatment.

FIG. 2A-FIG. 2F depict, in accordance with an embodiment of the invention, rapid 3-D delineation of nuclei in DAPI stained human cancer cells. Workflow in FIG. 2A) refers to example output images at mid-optical section of a z-stack: FIG. 2B) original image, FIG. 2C) preliminary mask of nuclei after background removal, FIG. 2D) output of 3-D radial symmetry transform obtained from the original image, FIG. 2E) seeds superimposed onto the original image, and FIG. 2F) delineated nuclei after final seed placement followed by seeded watershed segmentation.

FIG. 3A) view of the mid-section with 3 equiplanar spheres of different radii, FIG. 3B) profile through $S_r$ (with arbitrarily selected radial distance r=7), FIG. 3C) profile through S obtained via weighted aggregation of $S_{r=3}$, $S_{r=5}$, $S_{r=7}$, and $S_{r=9}$.

FIG. 4A-FIG. 4H depict, in accordance with an embodiment of the invention, an illustration of 3-D nuclei segmentation with subsequent processing steps: FIG. 4A) mid optical section of a 3-D image cube and FIG. 4B) final segmentation results. FIG. 4C) shows a close-up view of the upper-left quarter of FIG. 4A). Binary mask separating nuclei from background is shown in FIG. 4D), and the respective top-hat enhanced radial symmetry $\hat{S}$ in FIG. 4E). Seeds are marked in red. FIG. 4F) shows seed placement after the coarse step, and FIG. 4G) shows seeds detected in the fine mode. Bounding boxes (yellow) in FIG. 4F) indicate areas with clustered or in-close-proximity nuclei that were not separated by the seeded watershed segmentation. Clustered nuclei were recognized by shape and volume features and then pushed through the fine stage of seeds placement FIG. 4G). Seeds detected in FIG. 4G) replace seeds detected in FIG. 4F). Final nuclei delineation by the seeded watershed using seeds from FIG. 4G) is presented in FIG. 4H).

FIG. 7A-FIG. 7E depict, in accordance with an embodiment of the invention, a comparison of nuclei segmentation in a high confluency cell set from HuH-7 cell line treated with a high drug dose: FIG. 7A) original image, FIG. 7B) LSetCellTracker, FIG. 7C) Farsight, FIG. 7D) H-minima shape marking, and FIG. 7E) 3D-RSD method. Note over-segmentations in FIG. 7C) and under-segmentations and lack of detections (white arrows) in FIG. 7B) and FIG. 7D). The contrast inside of nuclei is weak. A large diversity of shape, degree of adjacency and staining intensity are prominent.

FIG. 8A-FIG. 8E depict, in accordance with an embodiment of the invention, a comparison of nuclei segmentation by different methods in moderate-to-high confluency cells set from Huh-7 cell line treated with a low drug dose: FIG. 8A) original image, FIG. 8B) LSetCelTrk, FIG. 8C) Farsight, and FIG. 8D) H-minima shape marking, and FIG. 8E) 3D-RSD method. Note heterogeneity of nuclear shape image contrast is slightly stronger when compared to that in FIG. 7A-FIG. 7E.

FIG. 9A-FIG. 9E depict, in accordance with an embodiment of the invention, a comparison of nuclei segmentation by different methods in low-to-moderate confluency cells set from untreated DU145 cell line: FIG. 9A) original image, FIG. 9B) LSetCellTracker, FIG. 9C) Farsight, FIG. 9D) H-minima shape marking, and FIG. 9E) 3D-RSD method. Note that some nuclei have more and some less intense staining.

DESCRIPTION OF THE INVENTION

Figure 3A:
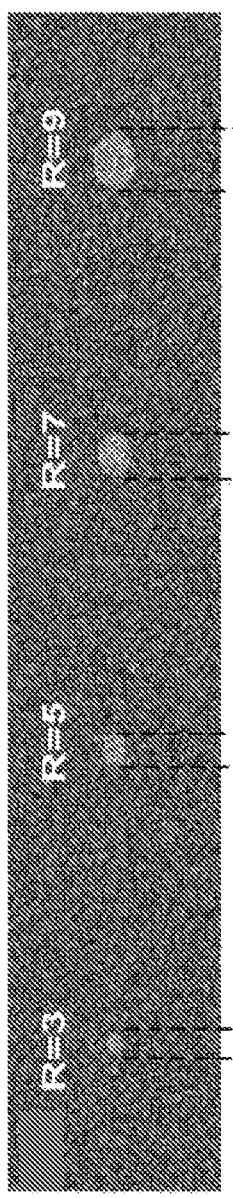
FIG. 3A-FIG. 3C depict, in accordance with an embodiment of the invention, example 3-D radial symmetry signals in an image with binary spheres with radii set to R=[3, 5, 7, 9] added to a noisy background with noise variance σ=0.25.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162): 323-7.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

"Mammal," as used herein, refers to any member of the class Mammalia, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term. The systems and methods for image analysis described herein can be utilized to analyze the cells of any animal, including any mammal.

"Treatment" and "treating," as used herein refer to both therapeutic treatment and prophylactic or preventative measures, wherein the object is to slow down (lessen) the condition, prevent the condition, pursue or obtain beneficial results, or lower the chances of the individual developing the condition, even if the treatment is ultimately unsuccessful. In some embodiments described herein, the systems and methods described herein for the analysis of cell images can lead directly or indirectly to the diagnosis, treatment, or monitoring of a disease, including, but in no way limited to cancer, metabolic disorders, and the like.

The inventors have developed new systems and methods for performing 3D radial symmetry detection (3D-RSD), to delineate nuclei by means of 3-D radial symmetries. These new systems and methods were tested on high-resolution image data of human cancer cells treated by drugs. The nuclei detection performance was evaluated by means of manually generated ground truth from 2351 nuclei (27 confocal stacks). When compared to three other nuclei segmentation methods, 3D-RSD possessed a better true positive rate of 83.3% and F-score of 0.895+/−0.045 (p-value=0.047). As described in greater detail herein below, altogether, 3D-RSD is a method with a very good overall segmentation performance. Furthermore, implementation of radial symmetries offers good processing speed, and makes 3D-RSD less sensitive to staining patterns. In particular the 3D-RSD method performs well in cell lines, which are often used in imaging-based HCS platforms that are afflicted by nuclear crowding and overlaps that hinder feature extraction. 2-D methods are also described herein in detail in the "Examples" section.

With the foregoing background in mind, in various embodiments, the invention teaches a method that includes delineating a nucleus of one or more cells in an image of one or more cells by utilizing a mathematical algorithm that is sensitive to the spherical shape of a nucleus of one or more cells in the image. In some embodiments, the method includes positioning/placing a seed within one or more cell nucleus in the image. In certain embodiments, the method includes applying watershed-based segmentation in which the positions of two or more seeds is considered during segmentation. In certain embodiments, one or more of the one or more cells have been stained with one or more markers. In various embodiments, one or more of the markers are fluorescent biomarkers. In some embodiments, one or more of the fluorescent biomarkers are immunofluorescent biomarkers. In various embodiments, at least one cell in the image has been immunolabeled with a 5-methylcytosine antibody and/or 4'6-diamidino-2-phenylindole (DAPI). In alternative embodiments, one or more cells could be stained with one or more markers that include, but are in no way limited to, Hoechst 33342 and Hoechst 33258, which are nuclear stains commonly used for nuclei counting in image cytometry. The purpose of these stains is almost identical to DAPI, but they are less toxic to cells and are therefore useful for imaging and tracking of live cells by confocal or ordinary microscopy. In fact, one of skill in the art would readily appreciate that practically any fluorescent stain that binds specifically to AT-rich regions of DNA (such as Hoechst, 33342 and Hoechst 33258 or DAPI) could be used in conjunction with the methods described herein. In certain embodiments, the image is acquired by confocal microscopy. In some embodiments, the image is acquired by high-resolution three-dimensional (3-D) confocal microscopy. In some embodiments, the image includes cells from a preparation of tissue mounted on a slide. In certain embodiments, at least one cell in the image is a cancer cell or pre-cancerous cell. In certain embodiments, at least one cell in the image is a cancer cell from a cancer cell line. In some embodiments, at least one cell in the image is a DU145 human prostate carcinoma cell. In some embodiments, at least one cell in the image is a HuH liver carcinoma cell. In some embodiments, at least one cell in the image is a cancerous cell (or precancerous cell) from a cancer type that may include, but is in no way limited to, prostate cancer, colorectal cancer, lung cancer, pancreatic cancer, stomach cancer, esophageal cancer, ovarian cancer, breast cancer, fallopian tube cancer, cervical cancer, brain cancer, liver cancer, and skin cancer (e.g. melanoma, basal cell carcinoma (BCC), squamous cell carcinoma (SCC)). In some embodiments, at least one cell in the image has been treated with a drug. In certain embodiments, the drug is a chemotherapeutic drug. In some embodiments, the cell nuclei delineation systems and methods described herein are utilized as part of a method for imaging-based high-content screening. In some embodiments, the cell-nuclei delineation systems and methods described herein can be utilized for analyzing changes in nuclear morphology, signal topology and signal co-localizations.

In various embodiments, the invention teaches a non-transitory computer-readable medium storing computer-readable instructions that, when executed by a processor of a computing device causes the computing device to perform steps including delineating a nucleus of one or more cells in an image of one or more cells by utilizing a mathematical algorithm that is sensitive to the spherical shape of a nucleus of one or more cells in the image. In some embodiments, the steps performed include delineating cell nuclei in an image by sequentially executed processing modules: a) preprocessing with background removal, b) 3-D radial symmetry detector followed by refinement of the symmetry signal, and c) adaptive seed placement with seed-controlled watershed segmentation of nuclei. Certain embodiments are described in greater detail in the examples set forth herein in the "examples" section. In certain embodiments, one or more of the one or more cells in the image have been stained with one or more markers. In various embodiments, one or more of the markers are fluorescent biomarkers. In some embodiments, one or more of the fluorescent biomarkers are immunofluorescent biomarkers. In various embodiments, at least one cell in the image has been immunolabeled with a 5-methylcytosine antibody and/or 4'6-diamidino-2-phenylindole (DAPI). In alternative embodiments, one or more cells could be stained with one or more markers that include, but are in no way limited to any of those described herein above. In certain embodiments, the image is acquired by confocal microscopy. In some embodiments, the image is acquired by high-resolution three-dimensional (3-D) confocal microscopy. In some embodiments, the image includes cells from a preparation of tissue mounted on a slide. In certain embodiments, at least one cell in the image is a cancer cell or pre-cancerous cell. In certain embodiments, at least one cell in the image is a cancer cell from a cancer cell line. In some embodiments, at least one cell in the image is a DU145 human prostate carcinoma cell. In some embodiments, at least one cell in the image is a HuH liver carcinoma cell. In some embodiments, at least one cell in the image has been treated with a drug. In certain embodiments, the drug is a chemotherapeutic drug. In some embodiments, at least one cell in the image is a cancerous cell (or precancerous cell) from a cancer type that may include, but is in no way limited to, prostate cancer, colorectal cancer, lung cancer, pancreatic cancer, stomach cancer, esophageal cancer, ovarian cancer, breast cancer, fallopian tube cancer, cervical cancer, brain cancer, liver cancer, and skin cancer (e.g. melanoma, basal cell carcinoma (BCC), squamous cell carcinoma (SCC)). In some embodiments, the cell nuclei delineation systems and methods described herein are utilized as part of a method for imaging-based high-content screening. In some embodiments, the cell-nuclei delineation systems and methods described herein can be utilized for analyzing changes in nuclear morphology, signal topology and signal co-localizations.

In various embodiments, the invention teaches a system configured to perform the methods described herein, wherein the system includes a confocal microscope (including but in no way limited to any type of confocal microscope described herein or in any reference cited herein) operably connected to (through physical or electronic communication) a computing device. The computing device may include, but is in no way limited to, a desktop computer, a laptop computer, or handheld computing device with sufficient computing capabilities to perform the methods described herein. In some embodiments, the computing device is specifically configured to perform the steps of one or more of the methods for image analysis set forth herein.

In some embodiments, the system includes a computing device with one or more processors; and one or more machine-readable media configured to store instructions that are executable by the one or more processors to perform any of the imaging operations described herein.

Figure 10:
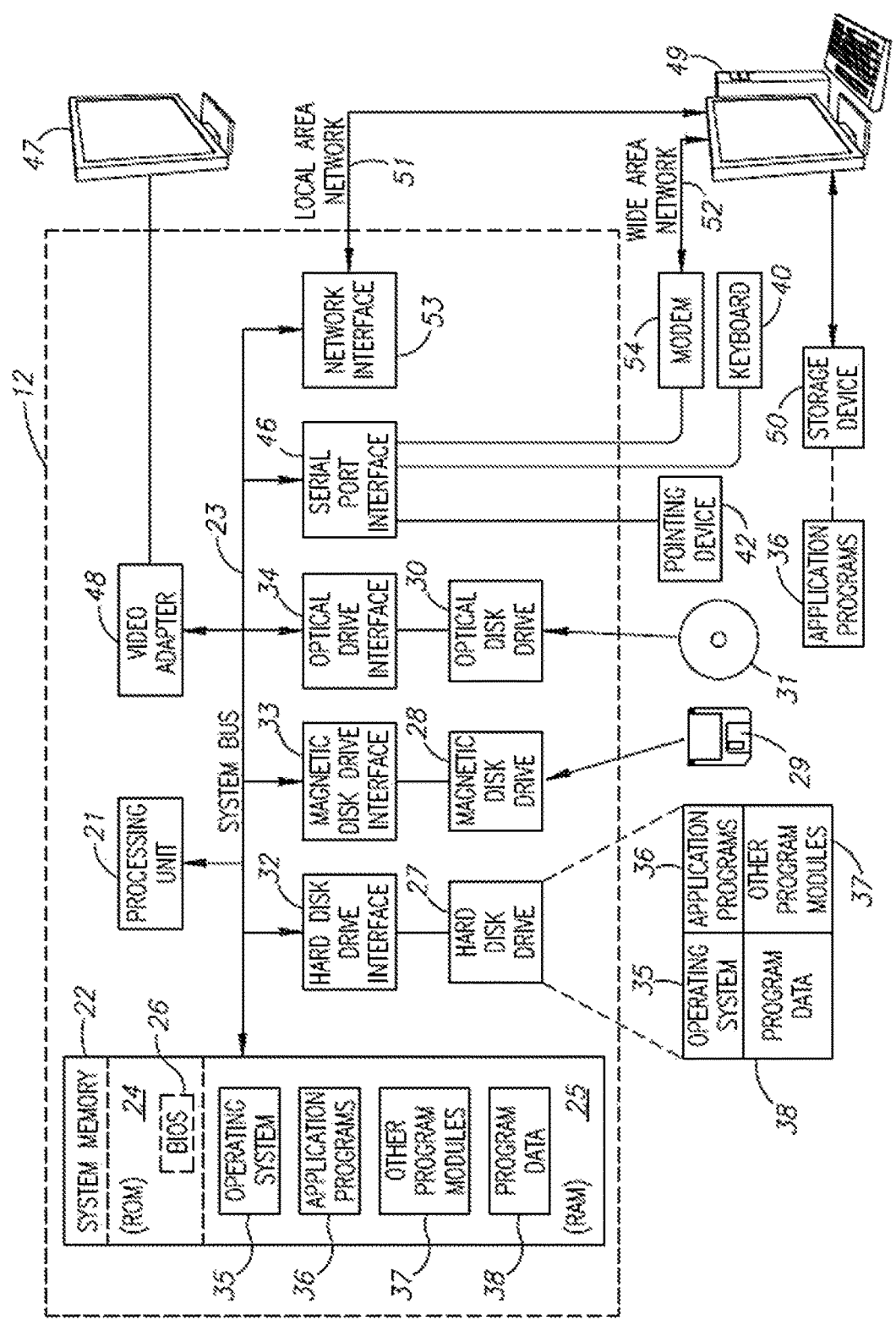
FIG. 10 depicts, in accordance with an embodiment of the invention, a diagram of hardware and an operating environment in conjunction with which implementations of a system's computing devices discussed herein may be practiced.

FIG. 10 is a diagram of hardware and an operating environment in conjunction with which implementations of the system's computing devices discussed herein may be practiced. The description of FIG. 10 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types.

Moreover, those skilled in the art will appreciate that implementations may be practiced with other computer system configurations, including hand-held devices, multi-processor systems, microprocessor-based or programmable consumer electronics, network PCs, minicomputers, mainframe computers, and the like. Implementations may also be practiced in distributed computing environments where tasks are performed by remote processing devices that are linked through a communications network. In a distributed computing environment, program modules may be located in both local and remote memory storage devices.

The exemplary hardware and operating environment of FIG. 10 includes a general-purpose computing device in the form of a computing device 12. Any of the aforementioned computing devices may each be implemented using one or more computing devices like the computing device 12.

The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. By way of a non-limiting example, such a heterogeneous processing environment may include a conventional CPU, a conventional graphics processing unit ("GPU"), a floating-point unit ("FPU"), combinations thereof, and the like. The computing device 12 may be a conventional computer, a distributed computer, or any other type of computer.

The system bus 23 may be any of several types of bus structures including a memory bus or memory controller, a peripheral bus, and a local bus using any of a variety of bus architectures. The system memory 22 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer-readable instructions, data structures, program modules, and other data for the computing device 12. It should be appreciated by those skilled in the art that any type of computer-readable media which can store data that is accessible by a computer, such as magnetic cassettes, flash memory cards, solid state memory devices ("SSD"), USB drives, digital video disks, Bernoulli cartridges, random access memories (RAMs), read only memories (ROMs), and the like, may be used in the exemplary operating environment. As is apparent to those of ordinary skill in the art, the hard disk drive 27 and other forms of computer-readable media (e.g., the removable magnetic disk 29, the removable optical disk 31, flash memory cards, SSD, USB drives, and the like) accessible by the processing unit 21 may be considered components of the system memory 22.

A number of program modules may be stored on the hard disk drive 27, magnetic disk 29, optical disk 31, ROM 24, or RAM 25, including an operating system 35, one or more application programs 36, other program modules 37, and program data 38. A user may enter commands and information into the computing device 12 through input devices such as a keyboard 40 and pointing device 42. Other input devices (not shown) may include a microphone, joystick, game pad, satellite dish, scanner, touch sensitive devices (e.g., a stylus or touch pad), video camera, depth camera, or the like. These and other input devices are often connected to the processing unit 21 through a serial port interface 46 that is coupled to the system bus 23, but may be connected by other interfaces, such as a parallel port, game port, a universal serial bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types physical feedback (e.g., a force feedback game controller).

The computing device 12 may operate in a networked environment using logical connections to one or more remote computers, such as remote computer 49. These logical connections are achieved by a communication device coupled to or a part of the computing device 12 (as the local computer). Implementations are not limited to a particular type of communications device.

The remote computer 49 may be another computer, a server, a router, a network PC, a client, a memory storage device, a peer device or other common network node, and typically includes many or all of the elements described above relative to the computing device 12. The remote computer 49 may be connected to a memory storage device 50. The logical connections depicted in FIG. 10 include a local-area network (LAN) 51 and a wide-area network (WAN) 52. Such networking environments are commonplace in offices, enterprise-wide computer networks, intranets and the Internet.

Those of ordinary skill in the art will appreciate that a LAN may be connected to a WAN via a modem using a carrier signal over a telephone network, cable network, cellular network, or power lines. Such a modem may be connected to the computing device 12 by a network interface (e.g., a serial or other type of port). Further, many laptop computers may connect to a network via a cellular data modem.

When used in a LAN-networking environment, the computing device 12 is connected to the local area network 51 through a network interface or adapter 53, which is one type of communications device. When used in a WAN networking environment, the computing device 12 typically includes a modem 54, a type of communications device, or any other type of communications device for establishing communications over the wide area network 52, such as the Internet. The modem 54, which may be internal or external, is connected to the system bus 23 via the serial port interface 46. In a networked environment, program modules depicted relative to the personal computing device 12, or portions thereof, may be stored in the remote computer 49 and/or the remote memory storage device 50. It is appreciated that the network connections shown are exemplary and other means of and communications devices for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality.

Various embodiments of the present invention are described in the ensuing examples. The examples are intended to be illustrative and in no way restrictive.

EXAMPLES

Example 1

By way of additional background, the objective and quantitative analysis of images from cells labeled with immunofluorescent probes takes microscopy from being purely visual, qualitative and subjective to a higher level. Quantitative analysis of fluorescently labeled molecular targets in cells can provide information of their spatial distribution, amounts and topology. The advantage of quantitative microscopy in cellular studies is further enhanced by the addition of automation. High-content screening (HCS)— or the automated acquisition of fluorescently labeled cellular images followed by an automated analysis enables the quantitative assessment of large numbers of images, thereby paving the way for large scale experiments in which multiple conditions are examined simultaneously, as described in Cox K L et al. Immunoassay Methods. In: *Assay Guidance Manual*. Edited by Sittampalam G S, et al. Bethesda (Md.); 2004; Buchser W, et al.: Assay Development Guidelines for Image-Based High Content Screening, High Content Analysis and High Content Imaging. In: *Assay Guidance Manual*. Edited by Sittampalam G S, et al. Bethesda (Md.); 2004; and Glory E and Murphy R F: Automated subcellular location determination and high-throughput microscopy. *Dev Cell* 2007, 12(1):7-16, all of which are hereby incorporated herein by reference in their entirety as though fully set forth. The scope of the technical applications of the present inventive technologies includes, but is in no way limited to, each of those described in the references set forth herein.

HCS platforms have primarily evolved as powerful approaches for drug discovery. Due to the involvement of high-resolution three-dimensional (3-D) confocal microscopy and multiplexing of fluorescent labels cell nuclei can be outlined and nuclear targets measured, rendering the cell nucleus the most frequently studied compartment. The 3-D screening turned out as a powerful tool for measurements of nuclear deformation, chromatin organization and cellular heterogeneity and essential in deriving deep, functional information involving spatial and temporal domains from single cells during response to drugs and assessment of cytotoxicity, as described in Bogusz A M, et al.: Quantitative Immunofluorescence Reveals the Signature of Active B-cell Receptor Signaling in Diffuse Large B-cell Lymphoma. *Clin Cancer Res* 2012, 18(22):6122-6135; and Kamykowski J, et al. Quantitative immunofluorescence mapping reveals little functional coclustering of proteins within platelet alpha-granules. *Blood* 2011, 118(5):1370-1373, both of which are hereby incorporated herein by reference in their entirety as though fully set forth.

The high automation of 3-D HCS necessitates image processing algorithms that can accurately and robustly analyze large numbers of images with little to no human intervention. In the automated processing pipelines the image segmentation is a front-end, yet most vulnerable numerical procedure. As a hardware and experimentally independent component, the image segmentation steps should be able to reliably separate nuclei from background and from each other. It is known that rapidly proliferating and overlapping cells provide a challenge for nuclei segmentation procedures. Variable nuclear shapes, chromatin texture, uneven image contrast and background noise increase the difficulty of delineating individual nuclei. A simple intensity based thresholding approach can often separate nuclei from background, unless they contact each other or are closely spaced. To achieve a reliable segmentation of nuclei, numerous semi-automated segmentation techniques have been published. However, many of them are tailored to a specific image analysis or screening method, or require the setting of multiple parameters. Fully automated methods are frequently restricted by the morphological variability of specimens, and thus allow only the analysis of regular or pre-selected patterns. Three larger groups for 3-D segmentation techniques can be distinguished and consist of: watershed-based, hybrid and deformable model-based segmentation techniques, as described in Harder N, et al.: Automatic analysis of dividing cells in live cell movies to detect mitotic delays and correlate phenotypes in time. *Genome Res* 2009, 19(11):2113-2124; Dzyubachyk O, et al.: Advanced level-set-based cell tracking in time-lapse fluorescence microscopy. *IEEE Trans Med Imaging* 2010, 29(3): 852-867; and Lin G, et al.: A multi-model approach to simultaneous segmentation and classification of heterogeneous populations of cell nuclei in 3D confocal microscope images. *Cytometry A* 2007, 71(9):724-736, all of which are hereby incorporated herein by reference in their entirety as though fully set forth.

While not wishing to be bound by any one particular theory, the latter is generally considered to be most reliable and requires little to no post-processing to refine the segmentation results. However, manual initializations and computational burden make them less practical for HCS analyses. Watershed-based techniques—especially those controlled by markers (seeds)—are computationally less intense, and hence generally faster. Yet, post-processing procedures tailored to the specimen's morphology are often necessary to determine if splitting or merging of closely positioned, clustered or contacting nuclei is required to correct over- and under-segmentations. Another family of nuclear segmentation advances utilizes geometric active contour approaches based on level-sets, as described in Dufour A, et al.: Segmenting and tracking fluorescent cells in dynamic 3-D microscopy with coupled active surfaces. *IEEE transactions on image processing: a publication of the IEEE Signal Processing Society* 2005, 14(9):1396-1410; Padfield D, et al.: Spatio-temporal cell cycle phase analysis using level sets and fast marching methods. *Medical image analysis* 2009, 13(1):143-155; and Wang M, et al.: Novel cell segmentation and online SVM for cell cycle phase identification in automated microscopy. *Bioinformatics* 2008, 24(1):94-101, all of which are hereby incorporated herein by reference in their entirety as though fully set forth. The level set method was originally used as a numerical technique for tracking shapes based on a variant of the geometric heat equation (as described in Malladi R and Sethian J A: Image processing via level set curvature flow. *Proc Natl Acad Sci USA* 1995, 92(15):7046-7050, which is hereby incorporated by reference herein in its entirety as though fully set forth), and it is meant to detect contours connecting pixels of the same intensity in an image. In the level set method, contours in 2-D or surfaces in 3-D can be represented by curves and surfaces on a Cartesian grid without the need to parameterize. The level set is able to represent the shapes even if their topology is complex. They are widely used since they do not require explicit parameterization. Yet, their main disadvantage is the computational cost. To separate objects (cells or nuclei), each object has to be represented by a level set function. In addition, a coupling constraint inhibits overlapping of neighboring contours. For N nuclei in the image, N level sets and $N^2$ coupling constraints are determined. These requirements dramatically increase the computational cost in highly confluent specimens. The method proposed by Dzubachyk et al. to segment and track cells by means of a coupled-active-surfaces framework can be used as an example of a level-set based technique (See Dzyubachyk O, et al.: Advanced level-set-based cell tracking in time-lapse fluorescence microscopy. *IEEE Trans Med Imaging* 2010, 29(3):852-867, which is hereby incorporated by reference herein in its entirety as though fully set forth). In their approach connected objects determined in the first image frame are segmented with one level-set function using a modified Chan and Vese algorithm, as described in Chan T F and Vese L A: Active contours without edges. *Image Processing, IEEE Transactions on* 2001, 10(2):266-277, which is hereby incorporated by reference in its entirety as though fully set forth. One level-set is assigned to each object. Each level-set function is iteratively evolved until convergence criteria are satisfied. Next, watersheds are used to perform rough splitting of level-set functions in connected components. The algorithm determines whether existing level-set functions need to be terminated or new functions introduced. In the final step, the Radon transform is applied to separate level-set functions of closely positioned nuclei. Tracking of cells is possible by propagating the final position of the level-sets from one image frame to another and adjusting the separation of the level-set functions accordingly.

Hybrid techniques for 2-D and 3-D nuclear segmentations such as those involving h-minima, h-maxima, or Laplacian-of-Gaussian filtering gradient or curvature analysis are better optimized for speed, automation and adaptability to new applications. A known example is the algorithm developed by Al-Kofahi and colleagues (See Al-Kofahi Y, et al.: Improved automatic detection and segmentation of cell nuclei in histopathology images. *IEEE Trans Biomed Eng* 2010, 57(4):841-852, which is hereby incorporated herein by reference in its entirety as though fully set forth). In this method the foreground-background separation through graph-cuts algorithm is subjected to seed detection using the scale normalized response of Laplacian-of-Gaussian constrained by the range of predefined scales. An initial segmentation of nuclei is obtained by the seed-based local-maximum clustering algorithm that allows separating the majority of clustered nuclei. The final segmentation is obtained through α-expansion and graph coloring. This method is built into FARSIGHT—a free platform for image analysis (see Bjornsson C S, et al.: Associative image analysis: a method for automated quantification of 3D multi-parameter images of brain tissue. *J Neurosci Methods* 2008, 170(1):165-178, which is hereby incorporated herein by reference in its entirety as though fully set forth). In Cheng et al geometric active contours were used to initially segment 2-D images, and then an adaptive H-minima-based algorithm was used to find shape markers that served as seeds for watershed-based splitting of closely spaced nuclei. Another published method involves a cascade of geometric filters insensitive to spatial non-uniformity coupled with geodesic level-sets, as described in Bilgin C C, et al.: Integrated profiling of three dimensional cell culture models and 3D microscopy. *Bioinformatics* 2013, 29(23):3087-3093, which is hereby incorporated by reference in its entirety as though fully set forth. It can partition clumped nuclei based on the grouping of points of maximum curvature that were combined according on their spatial properties to define planes dissecting clustered nuclei. Lastly, gradient methods described in Li G, et al.: 3D cell nuclei segmentation based on gradient flow tracking *BMC Cell Biol* 2007, 8:40; and Peng H, et al.: Extensible visualization and analysis for multidimensional images using Vaa3D. *Nat Protoc* 2014, 9(1):193-208, both of which are hereby incorporated herein by reference in their entirety as though fully set forth, employed a diffusion of gradients followed by tracking of their flow and grouping to identify individual nuclei in Zebrafish embryos.

Numerous other algorithms for 3-D image segmentation of cells and nuclei have been developed. While the majority are readily available for the analysis of non-complex cell images, there remains a deficiency of methods for imaging-based high-content screening that can deal with heterogeneity of nuclear texture and high confluency of cells. Such a method would enable screening and exploration of in-depth complex changes in nuclear morphology, signal topology, and signal co-localizations (see Zhao H, et al.: Biomarkers of cell senescence assessed by imaging cytometry. *Methods in molecular biology* 2013, 965:83-92; Brandhagen B N, et al.: Cytostasis and morphological changes induced by mifepristone in human metastatic cancer cells involve cytoskeletal filamentous actin reorganization and impairment of cell adhesion dynamics. *BMC cancer* 2013, 13:35; and Gertych A, et al.: Measuring topology of low-intensity DNA methylation sites for high-throughput assessment of epigenetic drug-induced effects in cancer cells. *Exp Cell Res* 2010, 316(19):3150-3160) (all of which are hereby incorporated herein by reference in their entirety as though fully set forth), which are all possible by utilizing the inventive technologies set forth herein.

As described herein in various embodiments, the present invention is directed to new approaches for rapid delineation of nuclei in high-resolution images. According to recent research, certain shape priors can be derived directly from the non-segmented image and funneled as features ahead of the actual nuclear segmentation routines. In certain embodiments, the present invention employs a 3-D radial symmetry transform followed by an adaptive post-processing of symmetry images to arrive at a mask of seeds that can guide a watershed-based segmentation. The output of the 3-D radial symmetry transform can quantitatively approximate the circularity of nuclei without an explicit knowledge about their localization. It can therefore serve as an input for guiding the image segmentation processes. In comparison to existing methods, this approach requires only a small set of shape descriptors such as circularity and radius upfront. This concept was developed and tested with synthetic images. High-resolution 3-D confocal images of human cells exposed to anticancer drugs were used to validate the effectiveness of the technique and its applicability to HCS. Performance was validated by comparing three state-of-the-art nuclear segmentation methods.

Materials

Image data was repurposed from an imaging-based high-content screening project (see Gertych A, et al. Measuring topology of low-intensity DNA methylation sites for high-throughput assessment of epigenetic drug-induced effects in cancer cells. *Exp Cell Res* 2010, 316(19):3150-3160; and Gertych A, et al.: 3-D DNA methylation phenotypes correlate with cytotoxicity levels in prostate and liver cancer cell models. *BMC pharmacology & toxicology* 2013, 14:11, both of which are hereby incorporated herein by reference in their entirety as though fully set forth) to characterize the potency of DNA methylation inhibitors in cancer cell lines. The material consisted of treated and untreated DU145 human prostate carcinoma cells, and HuH-7 liver carcinoma cells. Nuclei were immunolabeled with a 5-methylcytosine antibody and 4',6-diamidino-2-phenylindole (DAPI)—a common blue-fluorescent dye that intercalates into double stranded DNA. Staining was followed by confocal imaging. High-resolution optical sections with 1576×1576 pixels, voxel size of 120 nm×120 nm×250 nm (x-, y-, and z-axis) and 12 bits/pixel intensity depth were acquired to form 3-D stacks for each stain. 27 DAPI stacks that were generated on average from 35 slides (Tab.1) and represent a high variability of nuclear staining patterns and cell confluencies (FIG. 1) were selected from a large set of pre-existing image data to test the proposed methodology. More details related to specimens, drug treatment schedules, staining protocol and imaging can be found in Gertych A, et al.: Measuring topology of low-intensity DNA methylation sites for high-throughput assessment of epigenetic drug-induced effects in cancer cells. *Exp Cell Res* 2010, 316(19):3150-3160; and Gertych A, Oh J H, Wawrowsky K A, Weisenberger D J, Tajbakhsh J: 3-D DNA methylation phenotypes correlate with cytotoxicity levels in prostate and liver cancer cell models. *BMC pharmacology & toxicology* 2013, 14:11, both of which are incorporated herein by reference in their entirety as though fully set forth. Stacks were divided into three groups: low confluency with up to 40 nuclei per stack, moderate confluency (41-65 nuclei) and high confluency (73-190 nuclei). A cell biologist then manually identified and delineated 2351 nuclei (ground truth) in mid sections of the 27 stacks for segmentation performance assessment purposes.

TABLE 1

3-D image data characteristics.

| Cell line | Number of 3-D stacks | Confluency of nuclei (nuclear area/image area) | Average number of nuclei/stack |
|---|---|---|---|
| DU145 untreated | 10 | 20%-40% | 68 |
| DU145 treated | 9 | 18%-45% | 72 |
| HuH-7 treated | 8 | 55%-72% | 129 |

Methods

A non-limiting example of a nuclei segmentation method is described herein below and demonstrated in FIG. 2. Briefly, images were analyzed by sequentially executed processing modules: a) preprocessing with background removal, b) 3-D radial symmetry detector followed by refinement of the symmetry signal, and c) adaptive seed placement with seed-controlled watershed segmentation of nuclei. A preliminary mask after the background removal (FIG. 2C) served as a guide for seed placement. 3-D radial symmetry transform followed by post-processing with Gaussian smoothing and top-hat transform yielded radial symmetry images with high intensities localized at or near the centers of nuclei (FIG. 3D). The adaptive seed placement was run twice: in coarse (1) and fine (2) modes (FIG. 3E), and was responsible for probing the radial symmetry images and returning a single seed for each nucleus. User-specified morphometry features were entered to the algorithm to selectively screen and retain seeds with desired shape and volume. Seeds found within the preliminary mask were used by marker-controlled watershed segmentation. The coarse seed placement was run over the entire image, and was expected to detect seeds in closely adjacent nuclei. The fine seed placement was designed to find seeds of nuclei in a very closer proximity or forming clusters. An example output is shown in FIG. 3F.

Preprocessing with Background Removal

Preprocessing (FIG. 2A) was applied to remove the background and to suppress fluctuations of nonspecific DAPI staining seen as low-amplitude and low-frequency extra-nuclear signals. First, low-frequency components in the spectrum matrix obtained by the 3-D fast Fourier transform were shifted to the center, and coefficients inside an isotropic cube of size 3 in x, y and z direction superimposed onto the matrix center were turned to 0. Next, an intensity histogram was derived from the image reconstructed by the inverse 3-D fast Fourier transform. A parameter-free histogram thresholding (see Zack G W, et al.: Automatic measurement of sister chromatid exchange frequency. *The journal of histochemistry and cytochemistry: official journal of the Histochemistry Society* 1977, 25(7):741-753, which is incorporated herein by reference in its entirety as though fully set forth), was used to separate background (a narrow histogram peak) from nuclei staining (flat histogram tail). A preliminary mask P obtained in this manner (FIG. 2C) provided rough delineation of clustered and separated nuclei. P was then used to guide the detection of seeds and to further split nuclear clusters. To reduce the computational expense in the preprocessing step, the input image was down-sampled by a factor of four. P originating from the down-sampled image was then up-sampled to match the original size as shown in FIG. 2A.

3-D Radial Symmetry for Seed Detection

The concept of 3-D radial symmetry transform originates from the 2-D radial symmetry transform introduced as a context-free attentional operator to detect points of interest in facial images (see Loy G, Zelinsky A: Fast radial symmetry for detecting points of interest. *Ieee T Pattern Anal* 2003, 25(8):959-973, which is hereby incorporated herein by reference in its entirety as though fully set forth), and from its modified implementations for an automated detection of cell nuclei in images of cytological smears, as described in Gertych A, et al.: Automated detection of dual p16/Ki67 nuclear immunoreactivity in liquid-based Pap tests for improved cervical cancer risk stratification. *Ann Biomed Eng* 2012, 40(5):1192-1204; and Qin Y, et al.: Computerized delineation of nuclei in liquid-based Pap smears stained with immunohistochemical biomarkers. *Cytometry Part B, Clinical cytometry* 2014, both of which are hereby incorporated herein by reference in their entirety as though fully set forth. The 3-D radial symmetry can be obtained from image gradients after gradient magnitudes and orientations are accumulated in two separate matrices. By way of non-limiting example, in the 3-D application described here, the Sobel operator with a mask size of 3×3×3 was applied to provide image gradients in x, y and z direction. The depth related mask $G_Z$ was defined as:

$$G_Z = \begin{bmatrix} -2 & -4 & -2 \\ -4 & -8 & -4 \\ -2 & -4 & -2 \end{bmatrix}, \begin{bmatrix} 0 & 0 & 0 \\ 0 & 0 & 0 \\ 0 & 0 & 0 \end{bmatrix}, \begin{bmatrix} 2 & 4 & 2 \\ 4 & 8 & 4 \\ 2 & 4 & 2 \end{bmatrix}$$

whereas the two planar masks $G_X$ and $G_Y$ were respectively obtained by rotating $G_Z$ by 90 degrees around x and y axes traversing the center of the $G_Z$ mask. Gradients obtained through the masks' convolution with the original image were evaluated at each pixel p and its proximity defined by radius r. The contribution of image gradients pointing at $p^{(\circ)}(p)$ was accumulated in orientation projection $O_r$ and magnitude projection $M_r$ images. The voting-like technique (See Loy G, Zelinsky A: Fast radial symmetry for detecting points of interest. *Ieee T Pattern Anal* 2003, 25(8):959-973, which is incorporated herein by reference in its entirety as though fully set forth), which is a function of r, mapped the degree of object roundness at p considered as object centers. For bright objects overlaid on a dark background the corresponding pixels were evaluated as follows: $p^{(\circ)}(p)=p+\text{round}(r)\cdot \nabla I_{FOV}(p)/\|\nabla I_{FOV}(p)\|$, $O_r(p^{(\circ)}(p))=O_r(p^{(\circ)}(p))+1$, $M_r(p^{(\circ)}(p))=M_r(p^{(\circ)}(p))+\|\nabla I_{FOV}(p)\|$, where: round is the nearest integer rounding operator, $\|\nabla I_{FOV}(p)\|$ is the absolute gradient magnitude, and $\nabla I_{FOV}(p)/\|\nabla I_{FOV}(p)\|$ is the unit gradient at p.

In 2-D images analyzed in Loy G and Zelinsky A: Fast radial symmetry for detecting points of interest. *Ieee T Pattern Anal* 2003, 25(8):959-973; and Gertych A, Joseph A O, Walts A E, Bose S: Automated detection of dual p16/Ki67 nuclear immunoreactivity in liquid-based Pap tests for improved cervical cancer risk stratification. *Ann Biomed Eng* 2012, 40(5):1192-1204, both of which are hereby incorporated herein by reference in their entirety as though fully set forth, the magnitudes in $M_r$ were approximately two orders higher than those in $O_r$. In 3-D images analyzed here, the degree of discrepancy between $M_r$ and $O_r$ turned out to be much more prominent due to gradient components evaluated in all three dimensions. In order to balance the effect of the extent of discrepancy and the inherited nonlinearity of $M_r$ and $O_r$, a resulting radial voting image $F_r$ was formed as a weighted sum of the magnitude and projection images as follows:

$$F_r = |O_r(p)|k^\alpha + \alpha M_r(p) \tag{1}$$

where: k is the normalizing constant, and $\alpha$ serves as the scaling parameter. Low amplitude gradients attributed to non-round objects, line segments and noise in $O_r(p)$ were suppressed by normalizing $O_r(p)$ using k=10, and the radial strictness $\alpha=2$, as described in Loy G and Zelinsky A: Fast radial symmetry for detecting points of interest. *Ieee T Pattern Anal* 2003, 25(8):959-973, which is hereby incorporated herein by reference in its entirety as though fully set forth. Next, the 3-D voting image $F_r$ was smoothened by a Gaussian filter to obtain a 3-D radial symmetry image:

$$S_r = F_r * G_r \tag{2}$$

where:

$$G_r = \frac{1}{2\pi\sigma_{i,j}^2} e^{-\frac{i^2+j^2}{2\sigma_{i,j}^2}} \frac{1}{\sqrt{2\pi\sigma_k^2}} e^{-\frac{k^2}{2\sigma_k^2}}$$

is the Gaussian kernel, and i, j, k are the distances from the kernel origin along x, y and z axes respectively. Components of $G_r$ controlling the degree of smoothing were adjusted according to the voxel anisotropy of confocal sections, in which the ratio of planar resolution to the depth resolution was approximately 1:2. Hence, the smoothing coefficients were set as: $[\sigma_1, \sigma_1, \sigma_k] = [\frac{1}{2}r, \frac{1}{2}r, r]$ and $[i,j,k]=[r, r, \frac{1}{2}r]$ respectively. r is the radial distance, or simply the radius at which the gradients are evaluated. For isotropic voxels in synthetic images the respective settings were equal for all three dimensions.

Figure 3B:
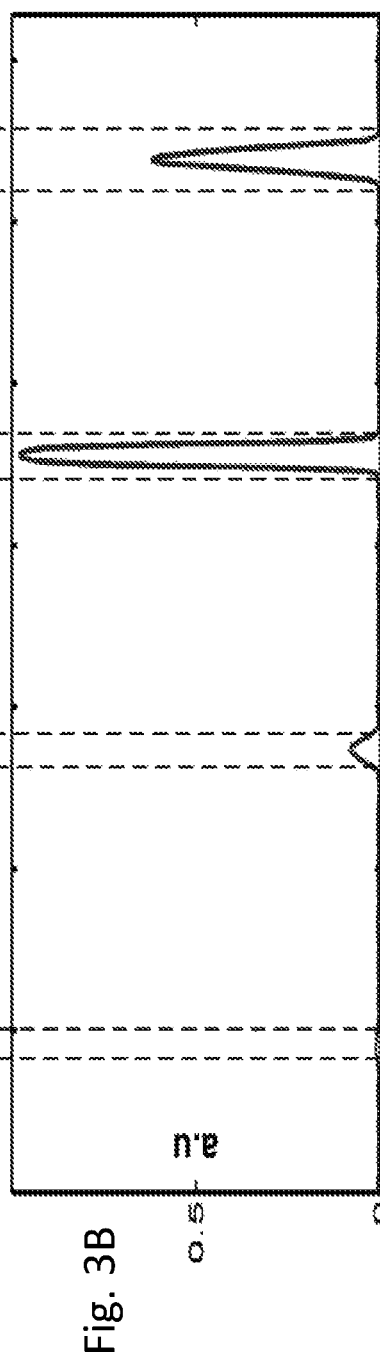

An artificial image was synthesized in order to demonstrate how the concept of the 3-D radial symmetry can benefit the automated detection of nuclei. Four binary spheres with incrementally increasing radii $R_i \in R=[3,5,7,9]$ with sphere centers aligned on the same z-plane (FIG. 3A) were added to a noisy background. For an arbitrarily chosen radial distance $r \in R$ an output image $S_r$ was calculated. An intensity profile (FIG. 3B) along a line passing through $S_r$ where the sphere centers were located demonstrates the shape and dynamics of symmetry signals. In this brief numerical experiment particular attention was paid to the shape, amplitude and location of peaks in $S_r$ defined here as local maxima: $\max(S_r(r,R))$. In particular: a) $S_r$ had high-amplitude and sharp peaks, b) all local maxima in $S_r$ corresponded to the location sphere centers, c) the magnitude of maxima in $S_r$ depended on the relationship between r and R: $\max(S_r(r=R_i,R)) > \max(S_r(r \ne R_i,R))$ (FIG. 3B). In other words, the closer r was to R the higher magnitude was observed, d) for any two spheres with radii $R_i \neq R_j$ and radial distances r matching the radii: max $(S_r(r=R_i,\{R_i, R_j\})) \neq$ max $(S_r(r=R_j, \{R_i, R_j\}))$. As a consequence of a)-e) if r was selected so that it closely corresponded to the radius of the target sphere, the local maximum was strong enough to be easily separated from background symmetries originating from noise.

Figure 3C:
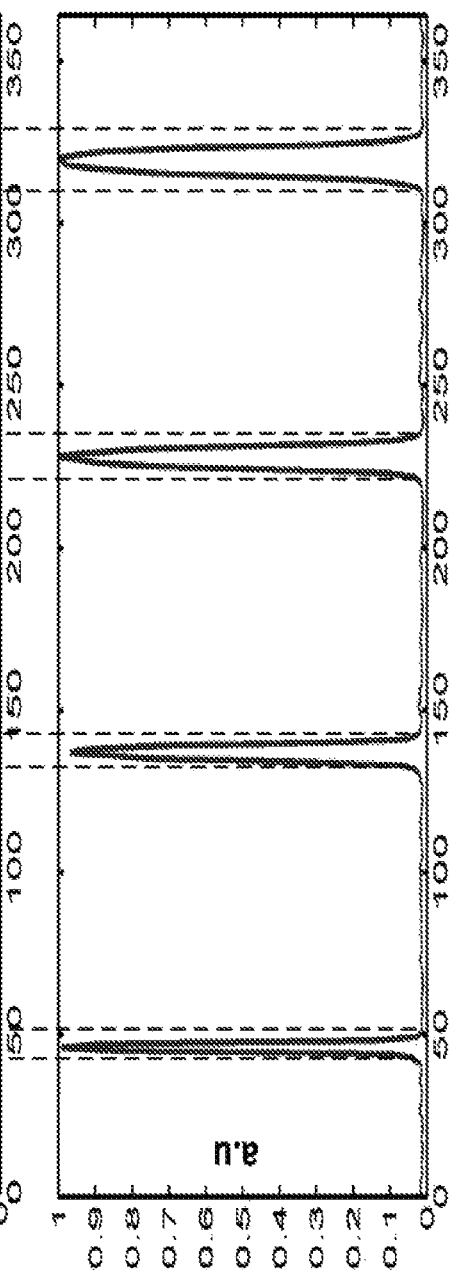

In the above context, r can be considered as an important parameter controlling magnitudes in $S_r$, and the way its peaks can be detected. Thus, by utilizing 3-D radial symmetries and some knowledge pertinent to the size of objects of interest it is possible to indicate the object's location. The next objective was to extend the above technique and calculate a series of $S_r$— one for each r from a priori given set of radii R, and analyze aggregated $S_r$s as a combined 3-D radial symmetry image in the following way:

$$\overline{S} = \Sigma_{r \in R} w_r S_r$$

$$w_r = c(\max(S_{r=R_i}))^{-1}$$

$$c = \max\{\max(S_{all\ r=R_i})\} \quad (3)$$

where: $w_r$ is the weight corresponding to single r, and c is the normalizing constant. Both $w_r$ and c can be derived from artificial images as in FIG. 3*a-b* to normalize the output for various r. Profiles traced throughout 3-D symmetry images aggregated in this manner are shown in FIG. 3C. For implementation in real images the weights $w_r$ were fixed as described in the "Seed detector properties and parameter settings for real images" section.

Top-Hat Transform

In contrast to ideal spheres evaluated in the artificial image shown in FIG. 1, the cell nuclei in confocal images have more arbitrary shapes and less definite centers. Moreover, nuclear texture can negatively contribute to orientation and magnitude of gradients related to the object's circularity, and collectively alter the shape of $\overline{S}$. Hence, the output of radial symmetry transform can be prone to coinciding shifts as well as widening and flattening of the radial symmetry peaks. 3-D top-hat transform (see Vincent L: Morphological grayscale reconstruction in image analysis: Applications and efficient algorithms. *Ieee T Image Process* 1993, 2(2):176-201, which is incorporated herein by reference in its entirety as though fully set forth) was implemented to alleviate this degradation, suppress local nonuniformities outside of main peaks in $\overline{S}$, and to better preserve the steepness of $\overline{S}$:

$$\hat{S} = \overline{S} - (\overline{S} \circ B) \quad (4)$$

where: $\circ$ is the gray-scale opening operator and B is the structuring element.

B was chosen to match the shape and volume of the largest object to be preserved. For anisotropic voxels an ellipsoidal neighborhood with size (r, r, r/2) along x, y and z-direction was set. For isotropic voxels the neighborhood size can be equal to r.

Adaptive Seed Placement (ASP) and Segmentation of Nuclei

Top-hat enhanced 3-D radial symmetry image $\hat{S}$ served as an input for the ASP to arrive at a mask of seeds. Importantly, in contrast to other seed placement techniques in which a seed was considered a spot that is significantly smaller than the object to be segmented, in this approach an ideal seed is meant to mark nearly the entire nuclear volume and follow as closely as possible the boundary of nuclear envelope. A systematic thresholding of $\hat{S}$ was implemented for this purpose. Thresholds t were determined between the min($\hat{S}$) and max($\hat{S}$) found in the radial symmetry image, and the range [min($\hat{S}$), max($\hat{S}$)] was split into a number of intervals that differed by a small constant A. The application of a single threshold t yielded a binary image $\hat{S}_b$ with multiple 3-D seed candidates that were automatically retained or rejected according to the following pseudo code:

---

ASP(Image, P, $\hat{S}$, $r_{min}$);

START:
    initialize variable:Seeds;
    t = min($\hat{S}$);
    repeat $$\hat{S}_b = \begin{cases} 1 & \text{if } \hat{S} \geq t \\ 0 & \text{otherwise} \end{cases};$$

Objects = Labeling($\hat{S}_b$);
    coarse: O = Objects with $(v_{Obj} \geq \frac{4}{3}\pi r_{min}^3) \subseteq P$;
    fine: O = Objects with $((v_{Obj} \geq \frac{4}{3}\pi r_{min}^3) \cap (circ_{Obj} \leq e_{xy}) \cap (solid_{Obj} \leq s_{hullxy})) \subseteq P$;
    Seeds = Seeds $\cup$ O;
    t = t + $\Delta$;
    until t > max($\hat{S}$);
STOP:

--- where: coarse and fine modes refer to the main workflow (FIG. 1), P is the preliminary mask of nuclei obtained during the preprocessing, $\hat{S}$ is the top-hat transform enhanced image, Objects is the variable storing seed candidates, $v_{Obj}$ is the volume of a seed candidate, $$circ_{Obj} = \frac{\text{Object major axis length}}{\text{Object minor axis length}} \text{ and } solid_{Obj} = \frac{\text{\# of Area pixels}}{\text{\# of Convex Area pixels}}$$

are the 2-D circularity and solidity features of a seed candidate calculated from the maximum intensity projection on the z-plane. $r_{min}$—is the smallest of the radii substituted to (2, 3), $e_{xy}$ and $s_{hullxy}$ are thresholds, n and U are the set intersection and sum, $\subseteq$ is the set inclusion operator, and Image is the input 3-D image. FIG. 4 illustrates in detail all processing steps including ASP (FIG. 4 F,G) along with example outputs obtained for a 3-D stack passing the whole workflow in FIG. 2. Binary seeds detected in the coarse mode were used in the marker-controlled watershed segmentation to delineate nuclei and nuclear clusters. Isolated nuclei and nuclear clusters segmented in this way were inspected to separate nuclei from clusters that were parsed to the fine mode. If the solidity of a cluster was lower than a predefined threshold $s_{hullxy}$ then a 3-D bounding box containing this cluster was extracted from a higher resolution image and pushed through the fine seed detection. If no more clusters meeting this criterion were found, the segmentation was completed.

Figure 5:
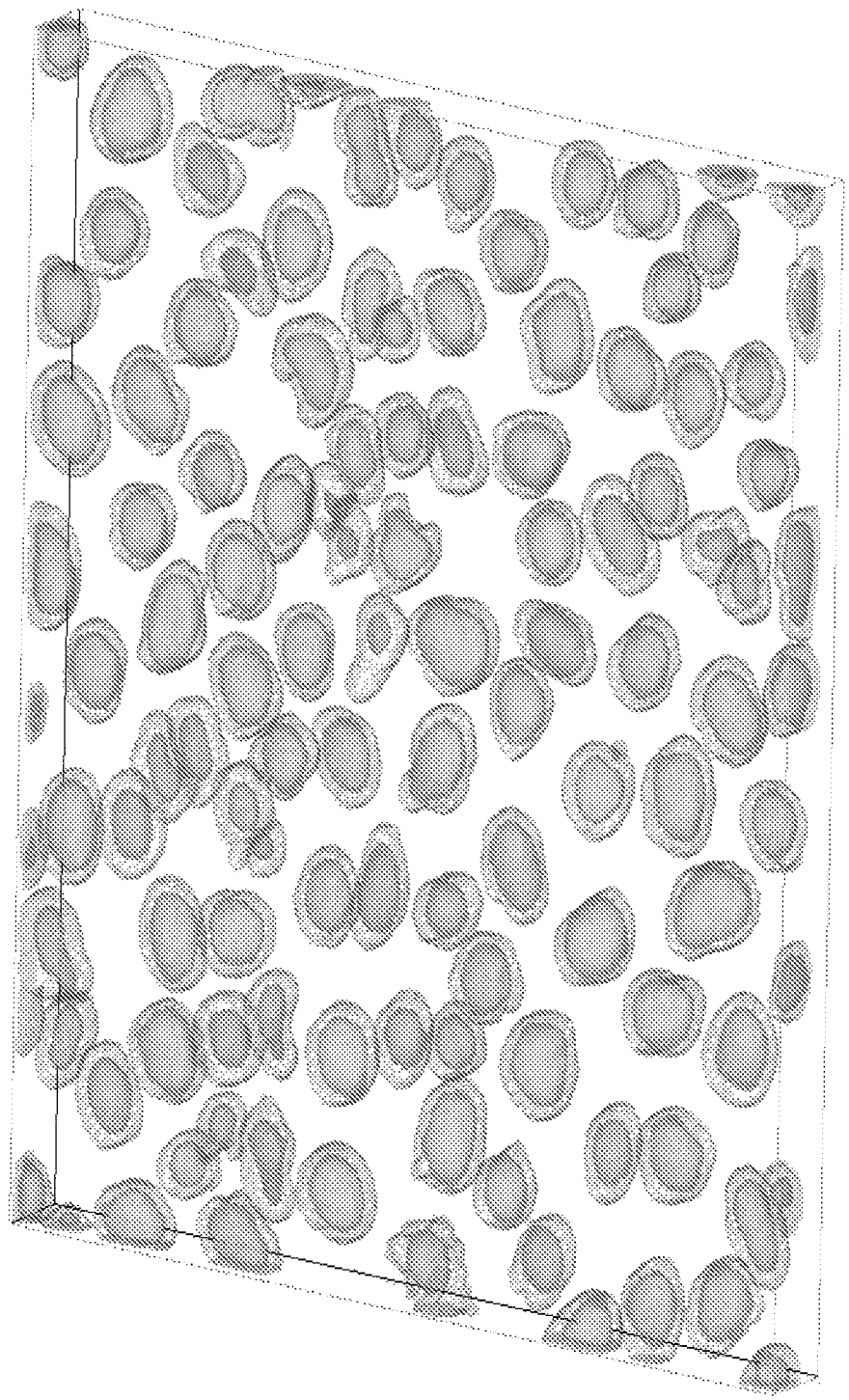
FIG. 5 depicts, in accordance with an embodiment of the invention, a 3D rendering of nuclei from FIG. 3: cyan— detected seeds, and gray—segmented nuclei. The rendering was obtained by means of an Image J volume rendering plugin.

The 3-D bounding box with clustered nuclei was subjected to fine analysis in which both the circularity and the solidity of seeds were checked in addition to the minimal seed volume. Any seed candidate with circularity and solidity smaller than $e_{xy}$ and $s_{hullxy}$ was rejected. Residual seeds replaced those determined in the coarse mode, and the 3-D bounding box was re-segmented by the seeded-watershed. Updated segmentation results were substituted to the final seed mask that was returned after all binary objects were examined (FIG. 3 B,H). Prior to running the ASP, the parameters such as radii, $s_{hullxy}$ and $e_{ey}$ were derived from randomly selected nuclei (as described in *Seed detector* properties and parameter settings for real images section) and embedded to the above pseudo code. An example final 3-D delineation of nuclei rendered using ImageJ plugin (see Schneider C A, et al.: NIH Image to ImageJ: 25 years of image analysis. *Nature methods* 2012, 9(7):671-675, which is hereby incorporated herein by reference in its entirety as though fully set forth) is shown in FIG. 5.

Seed Detector Properties and Parameter Settings for Real Images

In various embodiments, some prior knowledge related to nuclear morphology is required in order to properly utilize the proposed segmentation workflow. This includes nuclear radii and nuclear shapes. For that, manual delineation of 25 randomly selected nuclei from image data (FIG. 1, Tab.1) was performed. Images with delineated nuclei were downsampled to the two planar resolutions: 256×256 and 512×512 to reflect processing conditions in the coarse and fine modes. For each manually delineated nucleus and approximate radius was found. Radii from all nuclei (after rounding to nearest odd integers) were [3, 5, 7, 9, 11] and [9, 11, 13, 15] respectively for the two planar resolutions. Maximal values of solidity and circularity parameters were $s_{hullxy}=0.95$ and $e_{xy}=1.5$ as determined from 2-D maximum intensity projections of the manually delineated nuclei. $s_{hullxy}$ and $e_{xy}$ were same for both image resolutions. The radii and shape parameters were permanently embedded into the analytical workflow (FIG. 2).

Figure 6:
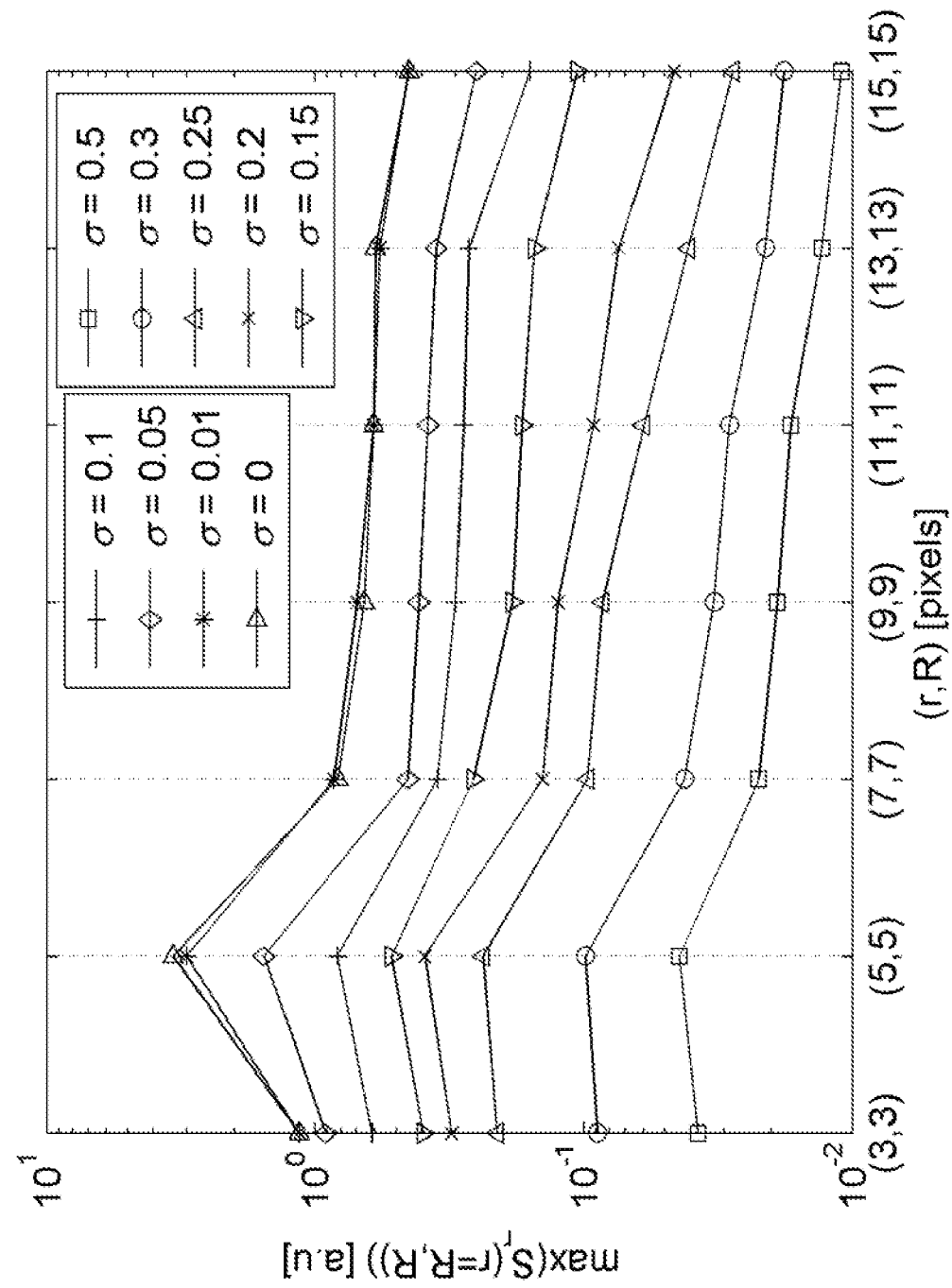
FIG. 6 depicts, in accordance with an embodiment of the invention, a 3-D radial symmetry response max($S_r$(r=R, R)) in an artificial image containing binary spheres with radii R∈[3,15]. Images were corrupted by additive Gaussian noise σ∈[0,0.5].

In addition, the involvement of multiple radii required weights $w_r$ (Equ.3) to be set to normalize amplitudes of radial symmetry images. These weights were analytically determined. The inventors extended the idea outlined in FIG. 3 and used a synthetic binary image containing seven spheres with radii $R \in [3,15]$—the same radii as those found in manually selected nuclei. The binary image was degraded by additive Gaussian noise with variance a that was gradually increased from 0 to 0.75. Radial symmetry images $S_r$ (Equ.2) were calculated and values $\max(S_r(r, R_i, \sigma)), \forall r=R_i$ were recorded. Highest magnitudes $\max(S_r(:))$ were observed in the center of each sphere consequently for every noise variance, and the increase of noise caused a progressive decline of $\max(S_r(:))$ (FIG. 6). However, the decline characteristics in the whole range of $r=R_i$ pairs of were similar regardless of the noise variance. This observation is important for the entire concept of 3-D radial symmetry based segmentation, because it allowed weights $w_r$ in (3) to be kept constant regardless of image degradation. For $\sigma>0.5$ and R, $r=3$ the $\max(S_r(:))$ was found outside of the sphere. Thus $\sigma>0.5$ and R, $r=3$ determine the theoretical limit of detection of 3D-RSD. For an uncorrupted image amplitude $\mu=1$ and $\sigma>0.5$ the lowest SNR=$\mu/\sigma$ at which the detection is possible is equivalent to SNR>2 (FIG. 6).

Ultimately, for the combined set of radii R=[5, 7, 9, 11, 13, 15] and an arbitrary selected noise level of $\sigma=0.05$, the following weights $w_r=1/[1.1, 0.8, 0.75, 0.55, 0.50, 0.44]$ were derived from FIG. 6. One can note that since the characteristics $\max(S_r(r,R_i,:))$ in FIG. 6 are similar there is a possibility to derive other sets of weights. Yet, their values will be proportional to those that were already selected. Thus, it was assumed that choosing the weights should have no impact on the segmentation as long as the ratios between the weights are preserved. The above selected weights were permanently embedded into the workflow.

Method Evaluation

The ground truth tracings were converted to binary masks. Following commonly used segmentation evaluation methods (see Coelho L P, et al.: Nuclear Segmentation in Microscope Cell Images: A Hand-Segmented Dataset and Comparison of Algorithms. Proc *IEEE Int Symp Biomed Imaging* 2009, 5193098:518-521; Qi J: Dense nuclei segmentation based on graph cut and convexity-concavity analysis. *Journal of microscopy* 2013; and Maska M, et al: A benchmark for comparison of cell tracking algorithms. *Bioinformatics* 2014, 30(11):1609-1617, all of which are hereby incorporated herein by reference in their entirety as though fully set forth) the precision=TP/(TP+FP), recall=TP/(TP+FN) (sensitivity), and F-measure: F=2*(precision*recall)/(precision+recall) were calculated to assess the performance. If the outline included <50% of the ground truth nuclear area, the result was counted as a FN (a miss), otherwise it was considered a TP. A lack of overlap with any ground truth was counted as a FP (an additional detection). In addition, the nuclear area agreement between the computed mask (C) and manual ground truth tracings (G) of all TP detections was evaluated by the Jaccard index:

$$J = \frac{\sum_w G \cap C}{\sum_w G \cup C};$$

where $\cap$ and $\cup$ represent the intersection and union of binary images, with the summation of involved pixels. Then, Jaccard indices from all nuclei in a 3-D image stack were averaged.

Four segmentation methods: Level Set Cell Tracker (LSetCellTracker) (see Dzyubachyk O, et al.: Advanced level-set-based cell tracking in time-lapse fluorescence microscopy. *IEEE Trans Med Imaging* 2010, 29(3):852-867, which is hereby incorporated herein by reference in its entirety as though fully set forth), Farsight (see Bjornsson C S, et al.: Associative image analysis: a method for automated quantification of 3D multi-parameter images of brain tissue. *J Neurosci Methods* 2008, 170(1):165-178, which is hereby incorporated herein by reference in its entirety as though fully set forth) ver. 0.4.4-win64 downloaded from www<dot>farsight-toolkit<dot>org/, 2-D H-minima shape marking method (see Jierong C and Rajapakse J C: Segmentation of Clustered Nuclei With Shape Markers and Marking Function. *Biomedical Engineering, IEEE Transactions on* 2009, 56(3):741-748, which is hereby incorporated herein by reference in its entirety as though fully set forth) that was adapted to process images in 3-D, and 3D-RSD were evaluated in this manner. Nuclei segmentation routines in Farsight are parameter-free, whereas the LSetCellTracker is equipped with a graphical user interface through which seven settings controlling the level set evolution namely $\alpha_0$, $\mu_0$, $t_0$ and H-minima for the initial segmentation step and $\alpha$, $\mu$, and $t$, for the main segmentation step can be manually adjusted. Since there are no guidelines on how to arrive at the most optimal set of parameters for this tool, H-minima was tuned (that is used to initially separate contacting objects) to 2 for which best results were obtained. The other parameters were kept default as no significant change in the segmentation performance after their adjustments were noticed. The 3-D H-minima shape marking method requires the gap parameter $\Delta$ to be set. Similarly to what is described in Jierong C and Rajapakse J C: Segmentation of Clustered Nuclei With Shape Markers and Marking Function. *Biomedical Engineering, IEEE Transactions on* 2009, 56(3): 741-748, which is incorporated herein by reference in its entirety as though fully set forth, its value was empirically determined and set permanently to $\Delta=2$ in the processing workflow that comprised background de-trending and removal from the processing pipeline and seeded-watersheds. A single set of parameters for 3D-RSD including radii, solidity and circularity was kept fixed permanently for all data sets. All stacks were downsampled to 512×512 pixels in the planar resolution to standardize processing and evaluation conditions for all three methods. 3D-RSD and LSetCellTracker and H-minima shape marking were coded in Matlab (Mathworks, Natick, Mass.). Farsight is a stand-alone application. All tests were run and timed on a PC-based 64-bit workstation computer.

Results

A performance evaluation was conducted utilizing 27 image 3-D stacks from two human cancer cell lines with highly variable nuclear staining patterns caused by drug treatment (Table. 1). Since nuclear confluence in image stacks varied (23 to 190 nuclei per stack), the testing set was split into three groups of low, moderate and high confluency and the performance of the three methodologies were tested, considering confluency as a variable. High confluency stacks constituted approximately 50% of all the data.

Quantitative evaluations pertinent to the TP, FP, and FN detection rates are shown in Table 2. The 3D-RSD method was the most sensitive across all the specimens (highest recall values) and yielded highest F-scores for data sets of low and high confluency. The paired two-sample t-test for F-scores was used to determine whether LSetCellTracker ($\mu_{Fscore}$=0.857, $\sigma_{Fscore}$=0.075), H-minima shape marking ($\mu_{Fscore}$=0.861, $\sigma_{Fscore}$=0.058) and 3D-RSD ($\mu_{Fscore}$=0.895, $\sigma_{Fscore}$=0.045) F-scores come from independent random samples (H0). The null hypothesis was rejected (p=0.035) and (p=0.047) at $\alpha$=0.05 strongly suggesting that 3D-RSD detected nuclei with significantly greater accuracy than LSetCellTracker and H-minima shape marking respectively. Farsight-based detections ($\mu_{Fscore}$=0.7412, $\sigma_{Fscore}$=0.267) were much worse compared to the other three methods. The area overlap metrics were also evaluated for all TP detections (Tab.3). TPs constituted 83.3%, 79.4%, 76.4% and 77.3% of the ground truth for 3D-FRST, H-minima shape marking, LSetCellTracker and Farsight, respectively. One-way ANOVA analysis of Jaccard indices showed no significant difference in contour delineation performance between Farsight, H-minima shape marking, and 3D-RSD, yet it indicted a statistical difference between these three methods and LSetCellTracker (which was best, p<0.0001). However, Farsight, H-minima shape marking and 3D-RSD analyzed stacks significantly faster than LSetCellTracker. FP detections by 3D-RSD were the lowest (75), compared to H-minima shape, LSetCellTracker, and Farsight, which respectively detected 119, 157 and 1724 additional false objects. In general, the segmentation rates were worse in low-contrast and highly confluent specimens. Example results for different cell confluencies are shown in FIGS. 7, 8 and 9 that were directly exported from the three tested methods as tiff files.

TABLE 2

Precision, recall and F-score for the four methods tested on 27 3-D stacks with variable nuclear confluence. Best rates are bolded.

| Confluency | Precision | | Recall | | F-score | |
|---|---|---|---|---|---|---|
| | low-moderate | high | low-moderate | high | low-moderate | high |
| 3D-RSD | 0.942 | 0.963 | 0.830 | 0.864 | 0.880 | 0.909 |
| LSetCelTrk | 0.936 | 0.908 | 0.862 | 0.763 | 0.893 | 0.824 |
| Farsight | 0.751 | 0.643 | 0.825 | 0.771 | 0.778 | 0.686 |
| H-minima shape marking | 0.898 | 0.931 | 0.795 | 0.836 | 0.838 | 0.878 |

TABLE 3

Jaccard indices and processing times of the four methods tested on 27 stacks.

| Confluency | Jaccard index | | | Average processing time [min] |
|---|---|---|---|---|
| | low | moderate | high | |
| 3D-RSD | 0.879 | 0.784 | 0.836 | 3.5 |
| LSetCelTrk | 0.958 | 0.954 | 0.891 | 153.2 |
| Farsight | 0.853 | 0.904 | 0.825 | 0.8 |
| H-minima shape marking | 0.851 | 0.773 | 0.827 | 2.0 |

Discussion

As speed and throughput of confocal imaging technology advance, reliable 3-D high-content analysis platforms are often sought to investigate cell phenotypes in cultures and tissue scaffolds. Particularly attractive is the opportunity to quantitatively characterize nuclear phenotypes in a high-content manner. Yet, image processing pipelines that can reliably quantify various cellular phenotypes are rare because developing a one-fits-all tool represents a significant challenge. For instance, CellProfiler (see Kamentsky L, et al.: Improved structure, function and compatibility for CellProfiler: modular high-throughput image analysis software. *Bioinformatics* 2011, 27(8):1179-1180, which is incorporated herein by reference as though fully set forth)—a commonly known platform can segment nuclei in a pseudo 3-D mode. Basically, in Cellprofiler's workflow a 3-D stack is considered as a series of 2-D images and therefore the segmentation of 2-D images one-by-one from top to bottom of the 3-D stack is performed. This approach necessitates the 3-D nuclear mask to be reconstructed from individual 2-D segmentations and may fail if either over-, under- or lack of segmentations in individual images occur.

Thus, many existing 3-D HCS solutions still fall short in terms of image analysis and speed and lack what is required to robustly navigate through multi-dimensional images. The majority of existing methods are adjusted to meet the parameters of a particular screening scenario and a more unified methodology to reliably segment nuclei in a variety of cellular specimens is one of the major goals in the bioimage informatics field.

Specimens that consist of highly confluent cells and crowded nuclei with heterogeneous textures in a background that is non-uniform and noisy are particularly difficult to analyze when they are imaged in 3-D at high-resolution. Published methods for their analysis are scarce. As indicated above, the examples described herein above are based on 3-D image data from an epigenetic drug evaluation study used to design and test a new nuclear segmentation procedure. Since some of the existing tools may not always perform well, 3-D radial symmetries were implemented to pinpoint nuclear regions of interest and to address the problem of nuclear segmentation in highly confluent and phenotype-dense image stacks. 3D-RSD was guided by the morphology of nuclei and arrived at a mask of seeds for watershed-based segmentation. Granted that the majority of cell nuclei were quasi spherical, the 3D-RSD successfully detected the circularity as the main feature in the image. In nuclear areas, 3D-RSD yielded a strong and high-affinity radial symmetry signal that was converted to large seeds and fitted into the boundary of the binary nuclear mask that was generated in the preprocessing step. Hence, the 3-D radial symmetries with selective characteristics can offer a new way to intuitively control seeded watershed segmentations. Importantly, the concept of seeds derived from radial votes described in Han J, et al.: Multiscale iterative voting for differential analysis of stress response for 2D and 3D cell culture models. *Journal of microscopy* 2011, 241(3):315-326, is different from the methods described here. The technique described in the examples set forth herein follows the early work by Loy et al (see Loy G and Zelinsky A: Fast radial symmetry for detecting points of interest. *Ieee T Pattern Anal* 2003, 25(8):959-973) and recent developments of radial symmetries for cervical smears, as described in Gertych A, et al.: Automated detection of dual p16/Ki67 nuclear immunoreactivity in liquid-based Pap tests for improved cervical cancer risk stratification. *Ann Biomed Eng* 2012, 40(5):1192-1204; and Qin Y, et al.: Computerized delineation of nuclei in liquid-based Pap smears stained with immunohistochemical biomarkers. *Cytometry Part B, Clinical cytometry* 2014, both of which are hereby incorporated herein by reference in their entirety as though fully set forth). In Han J, et al.: Multiscale iterative voting for differential analysis of stress response for 2D and 3D cell culture models. *Journal of microscopy* 2011, 241(3):315-326 the final landscape of iterative voting comes down to the localization of a center of mass—a small seed that constitutes a tiny fraction of the nuclear volume that is placed in the nucleus center. In contrast, in the examples described above (FIG. 4) the seeds are obtained through a radial symmetry image that is a weighted sum of orientation projection and magnitude projection images derived from local image gradients. Seeds obtained by the examples described herein are much larger and on average occupy 50% of the nuclear volume. Finally, the detected seeds are differently utilized for separation of nuclei in close contact or clusters. In Han et al. the partitioning of touching nuclei is based on Radon transform and Voronoi tessellation. In contrast, the methodology described herein employs watersheds. Importantly, as indicated above, large seeds significantly reduce the number of over segmented nuclei—an unwanted effect frequently observed in seeded-watershed algorithms that use punctate or small seeds.

The need for selection of image analysis parameters often prevents the implementation of full automation. User interactions are important to adjust parameters that control image segmentation (see Meijering E: Cell Segmentation: 50 Years Down the Road [Life Sciences]. *Signal Processing Magazine, IEEE* 2012, 29(5):140-145, which is hereby incorporated herein by reference in its entirety as though fully set forth), and it is challenging to develop setting-free methodologies that provide reliable outputs for all 3-D images. The 3D-RSD methods described in the examples above required a small set of pre-specified parameters as an input to guide the segmentation, which include radii, circularity and solidity, and are derived from a training sample of different nuclei. Unlike for the LevelSetCellTracker, the parameters for 3D-RSD were related to crude morphological features that are more intuitive to optimize for a less experienced user. More than 75% of nuclei were correctly segmented in the coarse pass of 3D-RSD. To improve the rates of segmentation in areas of high cell confluency, a fine mode was automatically used. The approach not only increased the TP detection rate to 83.3%, but also showed to be computationally efficient. Interestingly, the coarse and fine steps were involved solely in the detection and splitting of binary objects.

The numerical experiments involving 2351 human cells confirmed that the phenotype-dense specimens that exist in high-content screening studies (see Zhao H and Darzynkiewicz Z: Biomarkers of cell senescence assessed by imaging cytometry. *Methods in molecular biology* 2013, 965:83-92; and Gertych A, Farkas D L, Tajbakhsh J: Measuring topology of low-intensity DNA methylation sites for high-throughput assessment of epigenetic drug-induced effects in cancer cells. *Exp Cell Res* 2010, 316(19):3150-3160, both of which are hereby incorporated herein in their entirety as though fully set forth) can negatively affect the segmentation performances. Although the 3D-RSD was very robust in determining seeds for individual nuclei, the threshold-based background cutoff could be improved. In stacks with poor nucleus-to-background contrast such as those from experiments involving high levels of drug, this kind of preprocessing resulted in lower Jaccard index due to rougher nuclear contours versus the smooth ones yielded by LSetCellTracker. However, the two other methodologies which involved fundamentally different preprocessing algorithms were more compromised. Both Farsight and LSetCellTracker detected at least 6% fewer TP nuclei than 3D-RSD and had at least twice as high FP rates. Average performance of the H-minima shape marking that was directly adapted for 3-D processing was inferior to the methods described in the examples. Yet, it outperformed other methods in highly confluent specimens, and thus it seems that its modifications can further improve its seed detection capability.

Tests indicated that Farsight's detection rates varied while those from LSetCellTracker were more consistent. Since Farsight's nuclei segmentation algorithm is parameter free (parameters are fixed) it was not possible to investigate the exact cause of Farsight's low performance in images in question. While not wishing to be bound by any one particular theory, a possible reason for Farsight's over-segmentations in the image data could be the low contrast in nuclei pertinent to chromatin organization changes and the diversity of nuclear phenotypes in treated cells.

Collectively, it is appears that the inventive methodologies described herein are less sensitive to different experimental conditions such as: a) different cell lines, b) different treatment schedules, and c) different nuclear size and morphology than other methods tested. Specifically, 3D-RSD performed better in specimens in highly confluent specimens, including those that are affected by fluctuations of local contrast and local staining intensity induced by drugs. 3D-RSD is a method than can offer a very good overall segmentation performance without compromising processing speed—which is in high demand as a feature in imaging-based HCS platforms. Most importantly, the 3D-RSD utilizes local image gradients and provides an approximate localization of the target objects which other methods can utilize, and this important image feature can further be developed for analysis of other 3-D and 2-D nuclear and cell segmentation applications.

The inventive systems and methods address the issue of a rapid segmentation of nuclei towards fast and reliable phenotyping of large amount cells in 3-D cultures. As a user friendly—scalable and a relatively low complexity method the 3D-RSD achieved remarkable performances in cells lines treated by drugs. It is apparent that 3D-RSD can also be used for high-content screening tasks, including, but in no way limited to preclinical compound screening or image cytometry for cancer research. Accurate delineation is equivalent to tracing of a line around individual nuclei regardless of confluency of cells and nuclear staining intensity. When this procedure is done correctly, compartments of sub-nuclear structures such as nucleolus, eu- and heterochromatin and other nuclear bodies can be automatically delineated. In this way, quantification of immunofluorescent signals in the said compartments becomes possible. For example, heterochromatin that has been associated with gene regulation and chromosome integrity is found more commonly in the periphery of the nucleus attached to the nuclear membrane. Heterochromatic regions of DNA can be visualized by DAPI staining and immunofluorescence with antibodies against heterochromatin-binding proteins such as HP1. The visualization enables studying changes in heterochromatin condensation or tumor suppression gene functionality that occurs via heterochromatin-mediated silencing that can be drug targets. In case of inaccurate segmentation, the line is traced through the nuclei rather than around them. As a consequence, inaccurate delineation of the sub-nuclear compartments occurs erroneous quantification of immunofluorescence can take place.

Additional applications of the inventive technology may include a variety of 3-D single-cell based analyses. Merely by way of example the quantification of γH2AX expression and foci, which are found at regions of DNA damage, quantification of histone modifications which are involved in changes of heterochromatin formation, and in-vitro cytotoxicity assessment of drugs can be performed. In addition, target validation, and various tasks for localization and quantification of protein complexes in cells may benefit from a 3-D nuclei segmentation method.

Example 2

Figure 11:
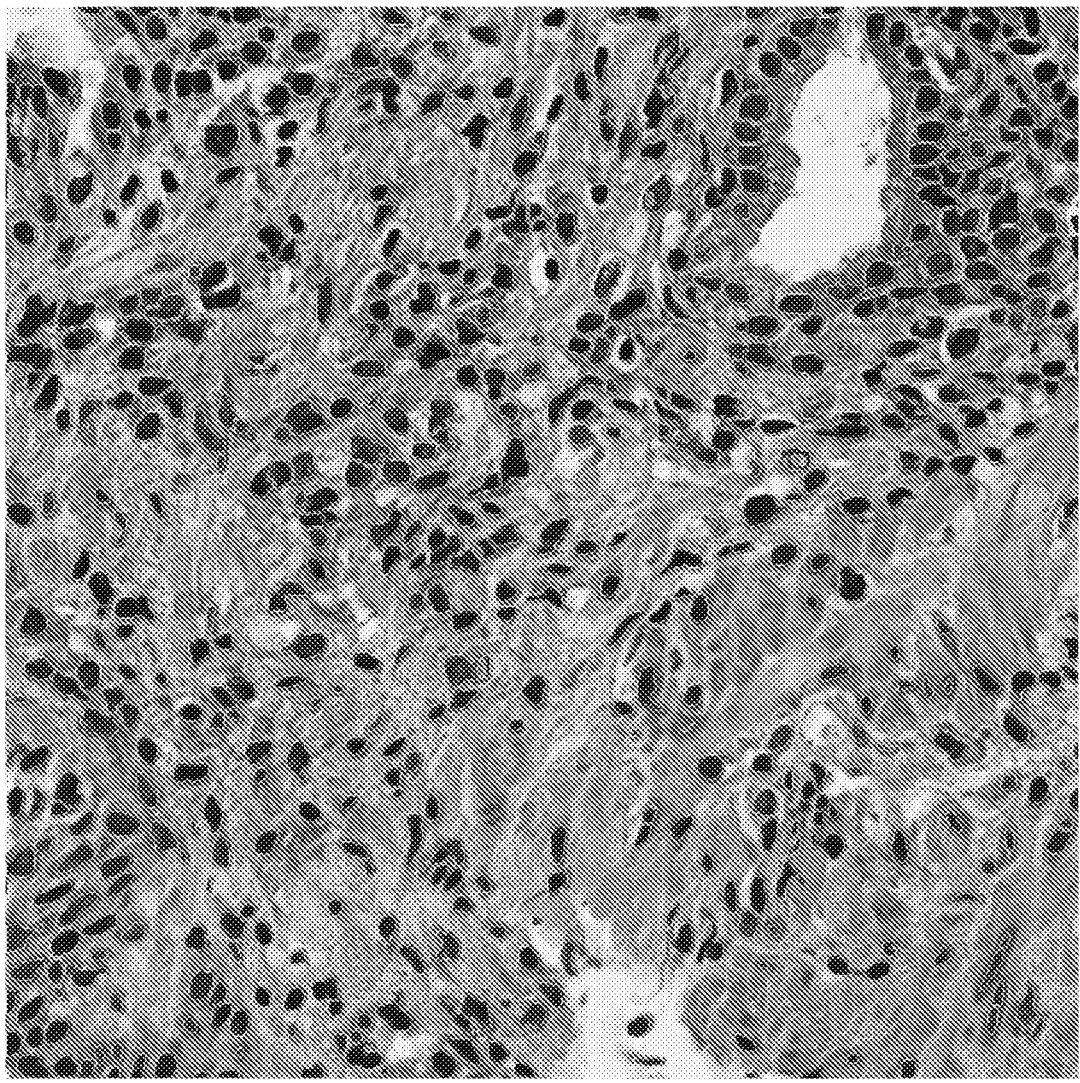
FIG. 11 depicts, in accordance with an embodiment of the invention, a micrograph of a high-grade prostate tumor. The tissue was stained with hematoxylin (blue color) that stains nuclei, and eosin (pink color) that stains eosinophilic structures of cells. Segmented nuclei are delineated by yellow lines. Note that some nuclei have more or less intense staining and that many nuclei have arbitrary shapes.
Figure 12:
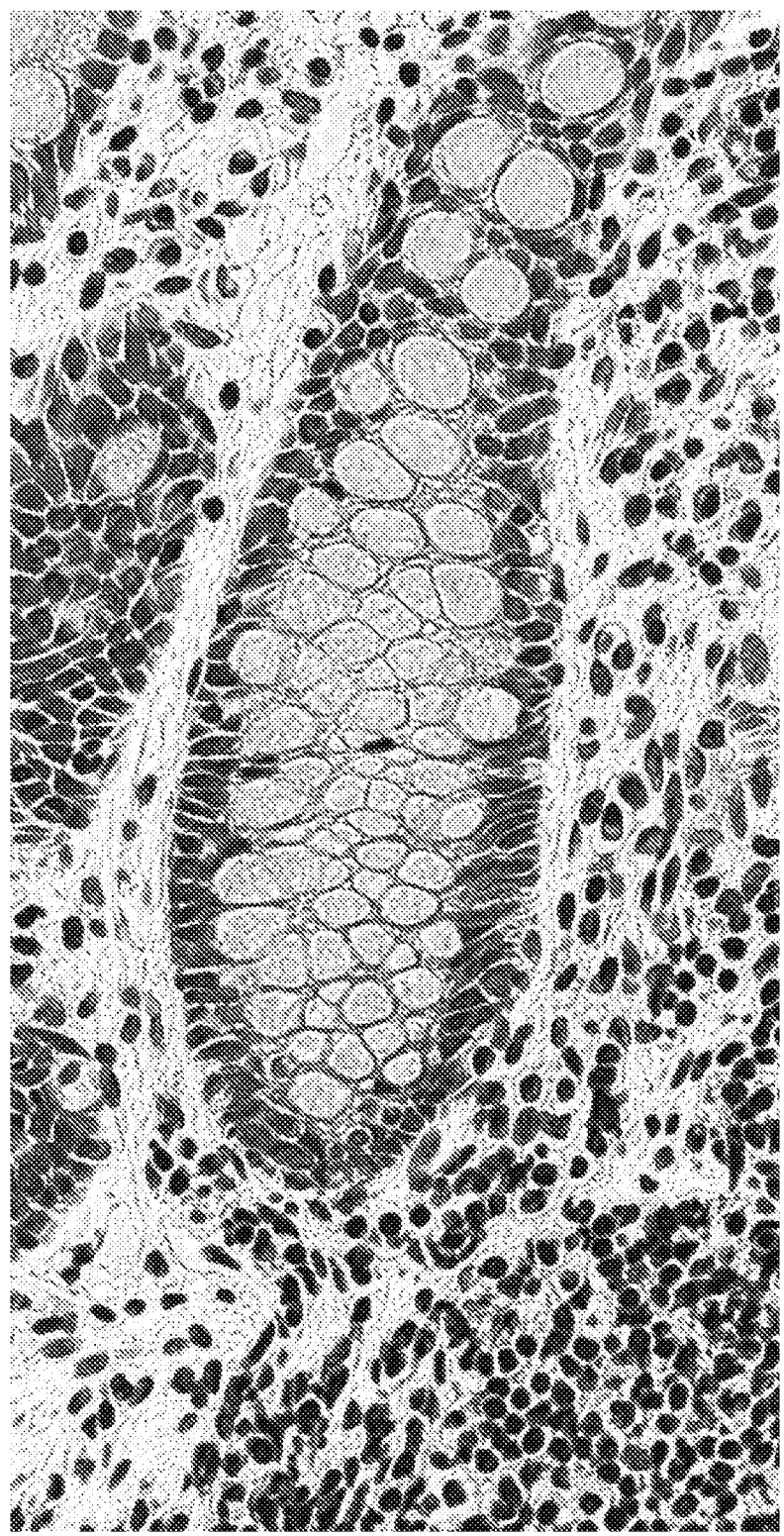
FIG. 12 depicts, in accordance with an embodiment of the invention, a gray-level micrograph of hematoxylin staining of human colon tissue. Segmented nuclei are delineated by red lines. Note that the tissue includes a variety of cell types including colon gland cells, immune cells and stromal cells and that each type is characterized by different shape, size and staining intensity. Note that this tissue contains areas of very-high, moderate and low cell confluency.

The results from another approach to delineating cell nuclei are demonstrated in FIGS. 11 and 12. In this approach two-dimensional color images of human tissues stained with hematoxylin and eosin were color-normalized and then color-deconvoluted to provide a monochromatic hematoxylin image for the segmentation of nuclei. Similarly to the 3D-RSD, a set of parameters namely the nuclear radii $R_i \in [5, 11]$ and nuclear shape defined by $s_{hullbxy}=0.95$ and $e_{xy}=1.5$ that was a priori defined. The nuclear mask was obtained by a parameter free histogram thresholding (see Zack G W, et al.: Automatic measurement of sister chromatid exchange frequency. *The journal of histochemistry and cytochemistry: official journal of the Histochemistry Society* 1977, 25(7): 741-753). The segmentation was then performed using the following sequence of routines: 2-D radial symmetry transform followed by the 2-D top-hat transform to obtain a radial symmetry image, and the adaptive seed placement followed by the 2-D seeded watershed to segment out individual nuclei under the nuclear mask. The 2-D radial symmetry transform constituted the core algorithm of a detector that can detect structures that are circular or semi-circular. The 2-D radial symmetry transform is computationally inexpensive and fast. Besides delineating nuclei in tissues (FIGS. 11 and 12) it can also be applied to the analysis of blood smears in hemo-pathology laboratory to screen for abnormal white blood cells.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method, comprising:
receiving 3D image stacks output from an imaging device comprising an image of one or more cells;
processing the 3D image stacks with a 3D radial symmetry transform to output radial symmetry images; and
processing the radial symmetry images to output images with segmented nuclei.

2. The method of claim 1, further comprising processing the radial symmetry images with adaptive seed placement to output a single seed for each nuclei.

3. The method of claim 2, wherein the radial symmetry images are a weighted sum of orientation projection and magnitude projection images derived from local image gradients.

4. The method of claim 3, further comprising applying watershed-based segmentation in which the positions of two or more seeds is considered during segmentation.

5. The method of claim 1, wherein one or more of the one or more cells has been stained with one or more markers.

6. The method of claim 5, wherein one or more of the markers are fluorescent biomarkers.

7. The method of claim 6, wherein one or more of the fluorescent biomarkers are immunofluorescent biomarkers.

8. The method of claim 1, wherein at least one cell in the image has been immunolabeled with a 5-methylcytosine antibody and/or 4'6-diamidino-2-phenylindole (DAPI).

9. The method of claim 1, wherein the image is acquired by confocal microscopy.

10. The method of claim 1, wherein the image comprises cells from a preparation of a tissue mounted on a slide.

11. The method of claim 1, wherein at least one cell in the image is a cancer cell or a pre-cancerous cell.

12. The method of claim 1, wherein at least one cell in the image has been treated with a drug.

13. The method of claim 12, wherein the drug is a chemotherapeutic drug.

* * * * *